(12) United States Patent
Dorwald et al.

(10) Patent No.: US 7,897,560 B2
(45) Date of Patent: Mar. 1, 2011

(54) PLASMA PROTEIN AFFINITY TAGS

(75) Inventors: Florencio Zaragoza Dorwald, Smorum (DK); Bernd Peschke, Malov (DK)

(73) Assignee: Novo Nordisk A/S, Bagsvaerd (DK)

( * ) Notice: Subject to any disclaimer, the term of this patent is extended or adjusted under 35 U.S.C. 154(b) by 664 days.

(21) Appl. No.: 11/384,129

(22) Filed: Mar. 17, 2006

(65) Prior Publication Data

US 2007/0105750 A1    May 10, 2007

Related U.S. Application Data

(63) Continuation of application No. PCT/DK2004/000625, filed on Sep. 17, 2004.

(60) Provisional application No. 60/505,501, filed on Sep. 24, 2003, provisional application No. 60/526,864, filed on Dec. 4, 2003.

(30) Foreign Application Priority Data

Sep. 19, 2003  (DK) ............................... 2003 01366
Dec. 4, 2003   (DK) ............................... 2003 01788

(51) Int. Cl.
  A61K 38/26   (2006.01)
  A61K 38/28   (2006.01)
  A61K 38/00   (2006.01)
  C07K 14/605  (2006.01)
  A61P 3/08    (2006.01)
  A61P 3/10    (2006.01)
  A61P 5/50    (2006.01)

(52) U.S. Cl. .................. 514/2; 514/3; 514/12; 514/13; 514/14; 514/15

(58) Field of Classification Search .................. None
See application file for complete search history.

(56) References Cited

U.S. PATENT DOCUMENTS

2004/0001827 A1   1/2004 Dennis

FOREIGN PATENT DOCUMENTS

| WO | 90/11296 | 10/1990 |
|----|----------|---------|
| WO | 98/08872 | 9/1997 |
| WO | 99/43341 | 2/1999 |
| WO | 99/43361 | 2/1999 |
| WO | 99/43705 | 2/1999 |
| WO | 99/43707 | 2/1999 |
| WO | 01/04156 | 7/2000 |
| WO | 01/51071 | 1/2001 |
| WO | 02/058725 | 1/2002 |
| WO | WO 02/46227 | 6/2002 |
| WO | 03/002136 | 1/2003 |
| WO | 03/087139 | 3/2003 |
| WO | 2004/074315 | 2/2004 |

OTHER PUBLICATIONS

Ngo JT, Marks J, Karplus M. "Computational Complexity, Protein Structure Prediction, and the Levinthal Paradox", The Protein Folding Problems and Tertiary Structure Prediction, K Merc, Jr. and S. Le Grand, Editors, Birkhauser Boston, 1994.*
Bradley CM, Barrick D. "Limits of Cooperativity in a Structurally Modular Protein: Response of the Notch ANkyrin Domain to Analogous Alanine Substitutions in Each Repeat", Journal of Molecular Biology, 2002, 324: 373-386.*
Rudinger J, "Characteristics of amino acids as components of a peptide hormone sequence," from Peptide Hormones, J.A. Parsons, MA, BM, B.Ch., University Park Press, Jun. 1976.*
"Designing Custom Peptides" from SIGMA Genosys, pp. 1-2. Accessed Dec. 16, 2004.*
Berendsen HJC, "A Glimpse of the Holy Grail?", Science, Oct. 23, 1998, 282: 642-643.*
Schinzel R and Drueckes P, "The phosphate recognition site of *Escherichia coli* maltodextrin phosphorylase," Federation of European Biochemical Society, Jul. 1991, 286(1,2): 125-128.*
Voet D and Voet JG, Biochemistry, Second Edition, John Wiley & Sons, Inc., 1995, pp. 235-241.*
Deacon, C.F. et al., Diabetologia, vol. 41, pp. 271-278 (1998).
Holz, G.G. et al., Curr Med Chem., vol. 10, pp. 2471-2483 (2003).
Knudsen, L.B. et al., J Med Chem., vol. 43, pp. 1664-1669 (2000).
Kurtzhals P. et al., Bio Chem, vol. 312(3), pp. 725-731 (1995).
Sheffield, W.P. et al., Curr Drug Targets Cardiovasc Haema., vol. 1(1), pp. 1-22 (2001).
Chuang VTG et al., Pharmaceutical Strategies Utilizing Recombinant Human Serum Albumin, Pharmaceutical Research, 2002, vol. 19, No. 5, pp. 569-577.
Han H-K, "Targeted Prodrug Design to Optimize Drug Delivery," AAPS Pharmsci, 2002, 2(1); 1-11.
Inflammatory Bowel Disease from e-Medicine, pp. 1-24, Accessed Sep. 24, 2008.
Kim, J-G et al., "Development and Characterization of a Glucagon-Like Peptide 1-Albumin Conjugate," Diabetes, 2003, 52: 751-759.
Pico, G., Studia Biophysica, 2000, vol. 136, No. 1, pp. 21-26.
Residue definition from www.dictionary.com, pp. 1-6, Accessed May 5, 2009.
Small Bowel Syndrome from e-Medicine, pp. 1-21, Accessed Sep. 24, 2008.
Zobel, K. et al., Bioorg Med Chem Lett., 2003, vol. 13, pp. 1513-1515.

* cited by examiner

*Primary Examiner*—Anish Gupta
*Assistant Examiner*—Julie Ha
(74) *Attorney, Agent, or Firm*—Richard W. Bork; Teresa A. Chen

(57) ABSTRACT

Method for increasing half-life of therapeutic agents in plasma and novel polypeptide derivatives.

20 Claims, No Drawings

```
                        SEQUENCE LISTING

<160> NUMBER OF SEQ ID NOS: 5

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 40
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa=L-histidine,D-histidine,desamino-histidine,
      2-amino-histidine,beta-hydroxy-histidine,homohistidine,
      N-alpha-acetyl-histidine,alpha-fluoromethyl-histidine,
      alpha-methyl-histidine,3-pyridylalanine,
      2-pyridylalanine, or 4-pyridylalanine
<220> FEATURE:
<221> NAME/KEY: MISC_FEATURE
<222> LOCATION: (2)..(2)
<223> OTHER INFORMATION: Xaa=Ala,Gly,Val,Leu,Ile,Lys,Aib,
      (1-aminocyclopropyl)carboxylic acid,
      (1-aminocyclobutyl)carboxylic acid,
      (1-aminocyclopentyl)carboxylic acid,
      (1-aminocyclohexyl)carboxylic acid,
      (1-aminocycloheptyl)carboxylic acid or
      (1-aminocyclooctyl)carboxylic acid
<220> FEATURE:
<221> NAME/KEY: MISC_FEATURE
<222> LOCATION: (10)..(10)
<223> OTHER INFORMATION: Xaa = Val or Leu.
<220> FEATURE:
<221> NAME/KEY: MISC_FEATURE
<222> LOCATION: (12)..(12)
<223> OTHER INFORMATION: Xaa = Ser, Lys or Arg.
<220> FEATURE:
<221> NAME/KEY: MISC_FEATURE
<222> LOCATION: (13)..(13)
```

```
<223> OTHER INFORMATION: Xaa = Tyr or Gln.
<220> FEATURE:
<221> NAME/KEY: MISC_FEATURE
<222> LOCATION: (14)..(14)
<223> OTHER INFORMATION: Xaa = Leu or Met.
<220> FEATURE:
<221> NAME/KEY: MISC_FEATURE
<222> LOCATION: (16)..(16)
<223> OTHER INFORMATION: Xaa = Gly, Glu or Aib.
<220> FEATURE:
<221> NAME/KEY: MISC_FEATURE
<222> LOCATION: (17)..(17)
<223> OTHER INFORMATION: Xaa = Gln, Glu, Lys or Arg.
<220> FEATURE:
<221> NAME/KEY: MISC_FEATURE
<222> LOCATION: (19)..(19)
<223> OTHER INFORMATION: Xaa = Ala or Val.
<220> FEATURE:
<221> NAME/KEY: MISC_FEATURE
<222> LOCATION: (20)..(20)
<223> OTHER INFORMATION: Xaa = Lys, Glu or Arg.
<220> FEATURE:
<221> NAME/KEY: MISC_FEATURE
<222> LOCATION: (21)..(21)
<223> OTHER INFORMATION: Xaa = Glu or Leu.
<220> FEATURE:
<221> NAME/KEY: MISC_FEATURE
<222> LOCATION: (24)..(24)
<223> OTHER INFORMATION: Xaa = Ala, Glu or Arg.
<220> FEATURE:
<221> NAME/KEY: MISC_FEATURE
<222> LOCATION: (27)..(27)
<223> OTHER INFORMATION: Xaa = Val or Lys.
<220> FEATURE:
<221> NAME/KEY: MISC_FEATURE
<222> LOCATION: (28)..(28)
<223> OTHER INFORMATION: Xaa = Lys, Glu, Asn or Arg.
<220> FEATURE:
<221> NAME/KEY: MISC_FEATURE
<222> LOCATION: (29)..(29)
<223> OTHER INFORMATION: Xaa = Gly or Aib
<220> FEATURE:
<221> NAME/KEY: MISC_FEATURE
<222> LOCATION: (30)..(30)
<223> OTHER INFORMATION: Xaa = Arg, Gly or Lys
<220> FEATURE:
<221> NAME/KEY: MISC_FEATURE
<222> LOCATION: (31)..(31)
<223> OTHER INFORMATION: Xaa = Gly, Ala, Glu, Pro, Lys, amide or is
      absent
<220> FEATURE:
<221> NAME/KEY: MISC_FEATURE
<222> LOCATION: (32)..(32)
<223> OTHER INFORMATION: Xaa = Lys, Ser, amide or is absent
<220> FEATURE:
<221> NAME/KEY: MISC_FEATURE
<222> LOCATION: (33)..(33)
<223> OTHER INFORMATION: Xaa = Ser, Lys, amide or is absent
<220> FEATURE:
<221> NAME/KEY: MISC_FEATURE
<222> LOCATION: (34)..(34)
<223> OTHER INFORMATION: Xaa = Gly, amide or is absent.
<220> FEATURE:
<221> NAME/KEY: MISC_FEATURE
<222> LOCATION: (35)..(35)
<223> OTHER INFORMATION: Xaa = Ala, amide or is absent.
<220> FEATURE:
<221> NAME/KEY: MISC_FEATURE
<222> LOCATION: (36)..(36)
<223> OTHER INFORMATION: Xaa = Pro, amide or is absent.
<220> FEATURE:
<221> NAME/KEY: MISC_FEATURE
<222> LOCATION: (37)..(37)
<223> OTHER INFORMATION: Xaa = Pro, amide or is absent.
<220> FEATURE:
<221> NAME/KEY: MISC_FEATURE
<222> LOCATION: (38)..(38)
<223> OTHER INFORMATION: Xaa = Pro, amide or is absent.
<220> FEATURE:
```

```
<221> NAME/KEY: MISC_FEATURE
<222> LOCATION: (39)..(39)
<223> OTHER INFORMATION: Xaa = Ser, amide or is absent.
<220> FEATURE:
<221> NAME/KEY: MISC_FEATURE
<222> LOCATION: (40)..(40)
<223> OTHER INFORMATION: Xaa = amide or is absent.

<400> SEQUENCE: 2

Xaa Xaa Glu Gly Thr Phe Thr Ser Asp Xaa Ser Xaa Xaa Xaa Glu Xaa
1               5                   10                  15

Xaa Ala Xaa Xaa Xaa Phe Ile Xaa Trp Leu Xaa Xaa Xaa Xaa Xaa Xaa
            20                  25                  30

Xaa Xaa Xaa Xaa Xaa Xaa Xaa Xaa
            35                  40

<210> SEQ ID NO 3
<211> LENGTH: 32
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa=L-histidine,D-histidine,desamino-histidine,
      2-amino-histidine,beta-hydroxy-histidine,homohistidine,
      N-alp,ha-acetyl-histidine,alpha-fluoromethyl-histidine,
      alpha-methyl-histidine,3-pyridylalanine,
      2-pyridylalanine, or 4-pyridylalanine
<220> FEATURE:
<221> NAME/KEY: MISC_FEATURE
<222> LOCATION: (2)..(2)
<223> OTHER INFORMATION: Xaa=Ala,Gly,Val,Leu,Ile,Lys,Aib,
      (1-aminocyclopropyl)carboxylic acid,
      (1-aminocyclobutyl)carboxylic acid,
      (1-aminocyclopentyl)carboxylic acid,
      (1-aminocyclohexyl)carboxylic acid,
      (1-aminocycloheptyl)carboxylic acid or
      (1-aminocyclooctyl)carboxylic acid.
<220> FEATURE:
<221> NAME/KEY: MISC_FEATURE
<222> LOCATION: (12)..(12)
<223> OTHER INFORMATION: Xaa = Ser, Lys or Arg.
<220> FEATURE:
<221> NAME/KEY: MISC_FEATURE
<222> LOCATION: (16)..(16)
<223> OTHER INFORMATION: Xaa = Gly, Glu or Aib.
<220> FEATURE:
<221> NAME/KEY: MISC_FEATURE
<222> LOCATION: (17)..(17)
<223> OTHER INFORMATION: Xaa = Gln, Gly, Lys or Arg.
<220> FEATURE:
<221> NAME/KEY: MISC_FEATURE
<222> LOCATION: (20)..(20)
<223> OTHER INFORMATION: Xaa = Lys, Glu or Arg.
<220> FEATURE:
<221> NAME/KEY: MISC_FEATURE
<222> LOCATION: (24)..(24)
<223> OTHER INFORMATION: Xaa = Ala, Glu or Arg.
<220> FEATURE:
<221> NAME/KEY: MISC_FEATURE
<222> LOCATION: (28)..(28)
<223> OTHER INFORMATION: Xaa = Lys, Glu or Arg.
<220> FEATURE:
<221> NAME/KEY: MISC_FEATURE
<222> LOCATION: (29)..(29)
<223> OTHER INFORMATION: Xaa = Gly or Aib.
<220> FEATURE:
<221> NAME/KEY: MISC_FEATURE
<222> LOCATION: (30)..(30)
<223> OTHER INFORMATION: Xaa = Arg or Lys.
<220> FEATURE:
<221> NAME/KEY: MISC_FEATURE
<222> LOCATION: (31)..(31)
```

```
<223> OTHER INFORMATION: Xaa = Gly, Ala, Glu or Lys.
<220> FEATURE:
<221> NAME/KEY: MISC_FEATURE
<222> LOCATION: (32)..(32)
<223> OTHER INFORMATION: Xaa = Lys, amide or is absent.

<400> SEQUENCE: 3

Xaa Xaa Glu Gly Thr Phe Thr Ser Asp Val Ser Xaa Tyr Leu Glu Xaa
1               5                   10                  15

Xaa Ala Ala Xaa Glu Phe Ile Xaa Trp Leu Val Xaa Xaa Xaa Xaa Xaa
            20                  25                  30

<210> SEQ ID NO 4
<211> LENGTH: 39
<212> TYPE: PRT
<213> ORGANISM: Gila monster

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 5
<211> LENGTH: 44
<212> TYPE: PRT
<213> ORGANISM: Artificial
<220> FEATURE:
<223> OTHER INFORMATION: Synthetic

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40
```

PLASMA PROTEIN AFFINITY TAGS

CROSS REFERENCE TO RELATED APPLICATIONS

This application is a continuation of International Application No. PCT/DK2004/000625, filed Sep. 17, 2004, which claims priority from Danish Patent Application Nos. PA 2003 01366 filed Sep. 19, 2003; PA 2003 01788 filed Dec. 4, 2003 and to U.S. Patent Application Nos. 60/505,501 filed Sep. 24, 2003; 60/526,864 filed Dec. 4, 2003.

FIELD OF THE INVENTION

The present invention relates to a new drug delivery system, based on novel compounds with high affinity to plasma proteins (=affinity tags). These affinity tags can be linked to therapeutically active compounds and thereby enhance their half-life in plasma by reversible binding to plasma proteins.

BACKGROUND OF THE INVENTION

It is often desirable to maintain well-defined concentrations of a given compound in the blood stream for a long time. This would for instance be the case when an immunogen is administered and a strong immune response is desired, or when a peripheral therapeutic target has to be exposed continuously to a therapeutic agent for a long time. Currently there are no universally applicable strategies to enhance the intravascular half-life of any type of compound.

The number of known endogenous peptides and proteins with interesting biological activities is growing rapidly, also as a result of the ongoing exploration of the human genome. Due to their biological activities, many of these peptides and proteins could in principle be used as therapeutic agents. Endogenous peptides are, however, not always suitable as drug candidates because these peptides often have half-lives of few minutes due to rapid degradation by peptidases and/or due to renal filtration and excretion in the urine. It has been shown by others (Zobel et al., *Bioorg. Med. Chem. Lett.* 2003, 13, 1513-1515) that the plasma half-life of a given peptide may be significantly enhanced by reversible attachment of this peptide to plasma proteins, such as albumin or gamma-globulin. Human serum albumin (HSA) has, for instance, a half-life of more than one week. This reversible attachment requires a compound (=affinity tag) which can be linked to the therapeutic agent, and which has a high binding affinity to albumin while bound to said therapeutic agent. Thus, generally applicable affinity tags would be of great general interest, in particular as potential drug-delivery systems.

Many of the most potent albumin-ligands known are carboxylic acids, such as fatty acids, arylacetic acids (e.g. ketoprofen), or iophenoxate, or dicarboxylic acids such as 3-carboxy-4-methyl-5-propyl-2-furanpropionic acid (CMPF) (Kratochwil et al. *Biochemical Pharmacology* 2002, 64, 1355-1374):

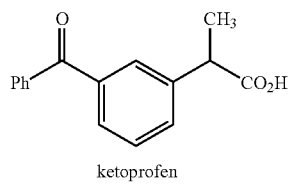

ketoprofen

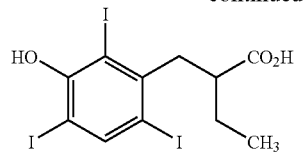

iophenoxate

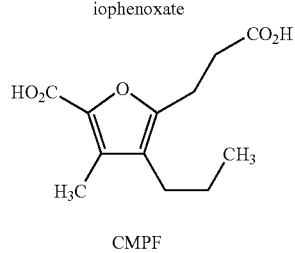

CMPF

All the structural features present in these compounds are, however, responsible for binding, and the affinity to HSA is lowered when these structural features are modified chemically. Thus, esters or amides of the acids mentioned above will have significantly lower affinities to HSA. The reason for this is that the carboxylic acid functionality forms strong ionic bonds with basic amino acids present in the plasma protein, and is therefore responsible to a large extent for the binding to the protein. Accordingly, it is not immediately obvious how to connect one of the known, strongly HSA-binding carboxylic acids to a therapeutic agent without loosing the required affinity to HSA. A method for achieving this would, however, be highly desirable, because many, structurally diverse carboxylic acids which bind to plasma proteins are already known, and no tedious screening for new compounds would be required. Furthermore, many of the known, HSA-binding carboxylic acids are currently marketed drugs, and their metabolites have been shown to be pharmaceutically and toxicologically acceptable.

The present invention intends to provide a versatile delivery system for therapeutic agents, such as proteins, peptides, or small molecule drugs, by covalently binding these therapeutic agents to a plasma-protein ligand, capable of reversible binding to one or several plasma proteins. We have designed a novel linking strategy which enables the covalent binding of known, plasma-protein binding carboxylic acids to a broad variety of therapeutic peptides or proteins, or to any other type of compound, of which a prolonged peripheral exposure at well-defined concentrations is required. This strategy consists in converting said plasma-protein binding carboxylic acid into a carboxylic acid mimetic, having a pKa between −5 and +7, in order to be ionized to a significant extent in plasma. Such a carboxylic acid mimetic could be, for instance, an N-acylsulfonamide, which contains an additional functional group which enables covalent binding of the acid mimetic to a therapeutic agent. This linking strategy should not significantly disturb the structure of the plasma-protein binding acid, if a suitable acid mimetic has been chosen. For instance, N-acylsulfonamides are similarly acidic as carboxylic acids, and will be deprotonated and negatively charged at physiological pH (B. J. Bakes, J. A. Ellman. *J. Am. Chem. Soc.* 1994, 116, 11171-11172).

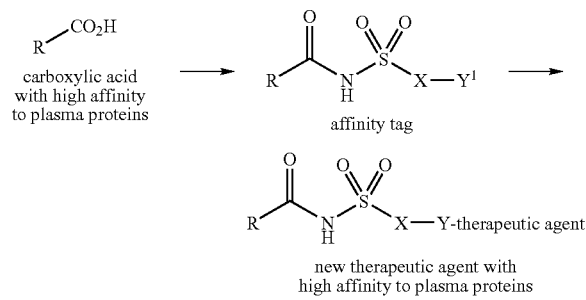

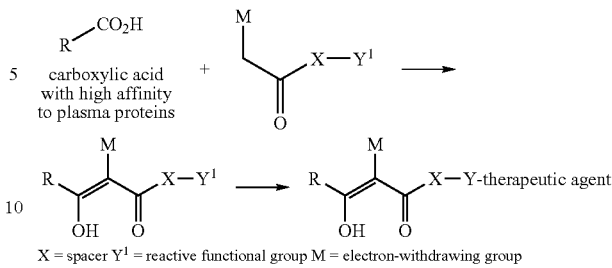

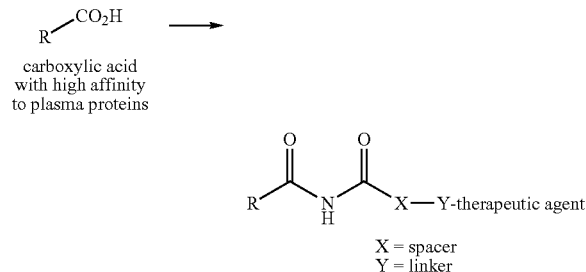

As illustrated by the sketches above, there may be an optional spacer X and a linker Y between the acid mimetic and the therapeutic agent for covalent attachment of the affinity tag to the therapeutic agent. These two groups will establish the distance between the plasma-protein binding fragment and the therapeutic agent. The linker Y can result from any reactive functional group $Y^1$ able to form a covalent, metabolically stable bond to the therapeutic agent which will not be cleaved at significant rates in vivo. Reactive groups $Y^1$ include, but are not limited to, carboxylic acids, amines, thiols, isothiocyanates, isocyanates, chloroformiates, O-succinimidyl carbonates, epoxides, sulfonyl chlorides, alkyl halides, electron-deficient alkenes, or other, related functional groups. Alternatively, the linker Y may also contain a metabolically labile bond, what would lead to a slow release of the untagged therapeutic agent in vivo. Such metabolically labile bonds are, for instance, present in certain carboxylic acid amides, disulfides, carboxylic esters, or carbamates.

Depending on the precise therapeutic target and on the length of the spacer X it may happen that the tagged therapeutic agent will exert its activity while bound to a plasma protein, or it could also happen that the tagged therapeutic agent will show a diminished biological activity while bound to the plasma protein, and only the unbound fraction of tagged therapeutic agent display the full biological activity. All these different features are included within the scope of the present invention.

Other carboxylic acid mimetics may, however, also be suitable for the purpose presented above. These include, for instance, imides, N-acylureas, and N-acylcarbamates.

Alternatively, acylated derivatives of electron-deficient, amino-substituted heterocycles or arenes may also be sufficiently acidic to be deprotonated in plasma, and are therefore also comprised within the scope of this invention.

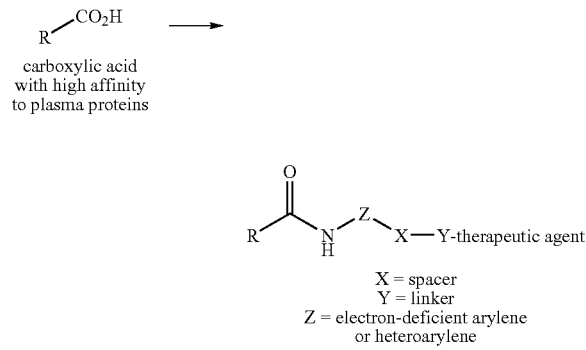

As a further alternative, carboxylic acids with a high affinity to a plasma protein may be used to C-acylate a cyano acetic acid derivative, a 3-ketocarboxylic acid derivative, or another acetic acid derivative with an electron-withdrawing group M attached to position 2. This group M could be, for example hydrogen, fluorine, —CN, —CO-alkyl, —CO-aryl, —CO$_2$-alkyl, —NO$_2$, —SO$_2$-aryl, —SO$_2$-alkyl, and the like. The resulting products would be strongly C—H-acidic and highly enolized, and could therefore also serve as carboxylic acid mimetic.

SUMMARY OF THE INVENTION

The present invention relates to a method of increasing the intravascular half-life of an agent, characterised by converting said agent into a compound of the general formula (I):

(I)

wherein
$R^1$ is the radical of carboxylic acid $R^1$—CO$_2$H, which $R^1$—CO$_2$H can bind reversibly to a plasma protein,
G is NH or CHW, wherein W is hydrogen, fluorine, cyano, nitro, C(=O)-E$^1$, S(=O)$_2$-E$^2$, S(=O)-E$^3$, aryl, or C$_{1-6}$alkyl,
  wherein E$^1$, E$^2$, and E$^3$ independently represent C$_{1-6}$alkyl, aryl, heteroaryl, C$_{1-6}$-alkoxy, amino, C$_{1-6}$alkyl-amino, or di-C$_{1-6}$alkyl-amino,
Z is S=O, S(=O)$_2$, C(=O), C(=O)O, C(=O)NR$^2$, or arylene which is optionally substituted with C$_{1-6}$alkyl, halogen, nitro, cyano, or heteroarylene, said heteroarylene optionally substituted with $C_{1-6}$-alkyl, halogen, nitro, or cyano, wherein $R^2$ represents hydrogen, cyano, or $C_{1-6}$alkyl, X represents a bond or a spacer, optionally selected from $C_1$-$C_{20}$-alkylene, arylene, heteroarylene, $C_1$-$C_{20}$-perfluoroalkylene, or combinations thereof, or $-[(CQ_2)_nA]_m(CQ_2)_p$-, or $-[(CQ_2)_nA]_m(CQ_2)_p-[(CQ_2)_nE]_m(CQ_2)_p$-, wherein n and m independently are 1-20 and p independently is 0-10, each A and E independently are —O—, —S—, —$NR^3$—, —N($COR^4$)—, —$PR^5$(O)—, -or P($OR^6$)(O)—, wherein $R^3$, $R^4$, $R^5$, and $R^6$ independently represent hydrogen or $C_{1-6}$alkyl, each Q is independently hydrogen or fluorine, Y represents a functional group capable of serving as linker to the agent, optionally selected from —C(=O)—, —C(=S)—, —$NR^7$(C=O)—, —OC(=O)—, —$NR^8$(C=S)—, —$CH_2$—, —CH(OH)—, —S(=O)$_2$—, —$NR^9$—S(=O)$_2$—, —S—, —S—S—, wherein $R^7$, $R^8$, and $R^6$ independently represent hydrogen or $C_{1-6}$alkyl, and the term 'agent' refers to the compound of which a prolonged half-life in plasma is desired.

The present invention also relates to a method of increasing intravascular half-live of a therapeutic agent, characterised by converting said therapeutic agent into a compound of the general formula (II):

$$R^1 \overset{O}{\underset{}{\|}} G^{\diagdown} Z^{\diagdown} X-Y\text{-therapeutic agent} \tag{II}$$

wherein $R^1$, G, Z, X, and Y are defined as described above.

The present invention also relates to a compound of the general formula (I):

$$R^1 \overset{O}{\underset{}{\|}} G^{\diagdown} Z^{\diagdown} X-Y\text{-agent} \tag{I}$$

wherein $R^1$ is the radical of carboxylic acid $R^1$—$CO_2H$, which $R^1$—$CO_2H$ can bind reversibly to a plasma protein, G is NH or CHW, wherein W is hydrogen, fluorine, cyano, nitro, C(=O)-$E^1$, S(=O)$_2$-$E^2$, S(=O)-$E^3$, aryl, or $C_{1-6}$-alkyl, wherein $E^1$, $E^2$, and $E^3$ independently represent $C_{1-6}$-alkyl, aryl, heteroaryl, $C_{1-6}$-alkoxy, amino, $C_{1-6}$-alkyl-amino, or di-$C_{1-6}$-alkyl-amino, Z is S=O, S(=O)$_2$, C(=O), C(=O)O, C(=O)$NR^2$, or arylene which is optionally substituted with $C_{1-6}$-alkyl, halogen, nitro, cyano, or heteroarylene, said heteroarylene optionally substituted with $C_{1-6}$-alkyl, halogen, nitro, or cyano, wherein $R^2$ represents hydrogen, cyano, or $C_{1-6}$-alkyl, X represents a bond or a spacer, optionally selected from $C_1$-$C_{20}$-alkylene, arylene, heteroarylene, $C_1$-$C_{20}$-perfluoroalkylene, or combinations thereof, or $-[(CQ_2)_nA]_m(CQ_2)_p$-, or $-[(CQ_2)_nA]_m(CQ_2)_p-[(CQ_2)_nE]_m(CQ_2)_p$-, wherein n and m independently are 1-20 and p independently is 0-10, each A and E independently are —O—, —S—, —$NR^3$—, —N($COR^4$)—, —$PR^5$(O)—, -or P($OR^6$)(O)—, wherein $R^3$, $R^4$, $R^5$, and $R^6$ independently represent hydrogen or $C_{1-6}$-alkyl, each Q is independently hydrogen or fluorine, Y represents a functional group capable of serving as linker to the agent, optionally selected from —C(=O)—, —C(=S)—, —$NR^7$(C=O)—, —OC(=O)—, —$NR^8$(C=S)—, —$CH_2$—, —CH(OH)—, —S(=O)$_2$—, —$NR^9$—S(=O)$_2$—, —S—, —S—S—, wherein $R^7$, $R^8$, and $R^6$ independently represent hydrogen or $C_{1-6}$-alkyl, and the term 'agent' refers to the compound of which a prolonged half-life in plasma is desired.

The present invention also relates to a compound of the general formula (II):

$$R^1 \overset{O}{\underset{}{\|}} G^{\diagdown} Z^{\diagdown} X-Y\text{-therapeutic agent} \tag{II}$$

wherein $R^1$, G, Z, X, and Y are defined as described above.

The present invention also relates to pharmaceutical compositions comprising a compound according to the present invention and the use of compounds according to the present invention for preparing medicaments for treating disease.

Definitions

In the present specification, the following terms have the indicated meaning:

The term "therapeutic agent" means a peptide, protein, small molecule drug, or any other type of compound, able to elicit a biological response.

The term "therapeutic polypeptide" as used herein means a polypeptide which is being developed for therapeutic use, or which has been developed for therapeutic use.

The term "polypeptide" and "peptide" as used herein means a compound composed of at least five constituent amino acids connected by peptide bonds. The constituent amino acids may be from the group of the amino acids encoded by the genetic code and they may natural amino acids which are not encoded by the genetic code, as well as synthetic amino acids. Natural amino acids which are not encoded by the genetic code are e.g. hydroxyproline, γ-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib (α-aminoisobutyric acid), Abu (α-aminobutyric acid), Tle (tert-butylglycine), β-alanine, 3-aminomethyl benzoic acid, anthranilic acid.

The term "analogue" as used herein referring to a polypeptide means a modified peptide wherein one or more amino acid residues of the peptide have been substituted by other amino acid residues and/or wherein one or more amino acid residues have been deleted from the peptide and/or wherein one or more amino acid residues have been deleted from the peptide and or wherein one or more amino acid residues have been added to the peptide. Such addition or deletion of amino acid residues can take place at the N-terminal of the peptide and/or at the C-terminal of the peptide. Two different and simple systems are often used to describe analogues: For example Arg[34]-GLP-1 (7-37) or K34R-GLP-1 (7-37) designates a GLP-1 analogue wherein amino acid residues at position 1-6 have been deleted, and the naturally occurring lysine at position 34 has been substituted with arginine (standard single letter abbreviation for amino acids used according to IUPAC-IUB nomenclature).

The term "derivative" as used herein in relation to a peptide means a chemically modified peptide or an analogue thereof, wherein at least one substituent is not present in the unmodified peptide or an analogue thereof, i.e. a peptide which has been covalently modified. Typical modifications are amides, carbohydrates, alkyl groups, acyl groups, esters and the like. An example of a derivative of GLP-1(7-37) is Arg[34], Lys[26] ($N^\epsilon$-($\gamma$-Glu($N^\alpha$-hexadecanoyl)))-GLP-1(7-37).

The term "GLP-1 peptide" as used herein means GLP-1(7-37), a GLP-1 analogue, a GLP-1 derivative or a derivative of a GLP-1 analogue. In one embodiment the GLP-1 peptide is an insulinotropic agent.

The term "insulinotropic agent" as used herein means a compound which is an agonist of the human GLP-1 receptor, i.e. a compound which stimulates the formation of cAMP in a suitable medium containing the human GLP-1 receptor. The potency of an insulinotropic agent is determined by calculating the $EC_{50}$ value from the dose-response curve as described below.

Baby hamster kidney (BHK) cells expressing the cloned human GLP-1 receptor (BHK-467-12A) were grown in DMEM media with the addition of 100 IU/mL penicillin, 100 μL/mL streptomycin, 10% fetal calf serum and 1 mg/mL Geneticin G-418 (Life Technologies). Plasma membranes were prepared by homogenisation in buffer (10 mM Tris-HCl, 30 mM NaCl and 1 mM dithiothreitol, pH 7.4, containing, in addition, 5 mg/L leupeptin (Sigma, St. Louis, Mo., USA), 5 mg/L pepstatin (Sigma), 100 mg/L bacitracin (Sigma), and 16 mg/L aprotinin (Calbiochem-Novabiochem, La Jolla, Calif.). The homogenate was centrifuged on top of a layer of 41 w/v % sucrose. The white band between the two layers was diluted in buffer and centrifuged. Plasma membranes were stored at −80° C. until used. The functional receptor assay was carried out by measuring CAMP as a response to stimulation by the insulinotropic agent. Incubation were carried out in 96-well microtiter plates in a total volume of 140 μL and with the following final concentrations: 50 mM Tris-HCl, 1 mM EGTA, 1.5 mM $MgSO_4$, 1.7 mM ATP, 20 mM GTP, 2 mM 3-isobutyl-1-methylxanthine (IBMX), 0.01% Tween-20, pH 7.4. Compounds to be tested for agonist activity were dissolved and diluted in buffer. GTP was freshly prepared for each experiment: 2.5 μg of membrane was added to each well and the mixture was incubated for 90 min at room temperature in the dark with shaking. The reaction was stopped by the addition of 25 μL of 0.5 M HCl. Formed CAMP was measured by a scintillation proximity assay (RPA 542, Amersham, UK). Dose-response curves were plotted for the individual compounds and $EC_{50}$ values calculated using GraphPad Prism software.

The term "GLP-2 peptide" as used herein means GLP-2(1-33), a GLP-2 analogue, a GLP-2 derivative or a derivative of a GLP-2 analogue.

The term "exendin-4 peptide" as used herein means exendin-4(1-39), an exendin-4 analogue, an exendin-4 derivative or a derivative of an exendin-4 analogue. In one embodiment the exendin-4 peptide is an insulinotropic agent.

The term "DPP-IV protected" as used herein referring to a polypeptide means a polypeptide which has been chemically modified in order to render said compound resistant to the plasma peptidase dipeptidyl aminopeptidase-4 (DPP-IV). The DPP-IV enzyme in plasma is known to be involved in the degradation of several peptide hormones, e.g. GLP-1, GLP-2, Exendin-4 etc. Thus, a considerable effort is being made to develop analogues and derivatives of the polypeptides susceptible to DPP-IV mediated hydrolysis in order to reduce the rate of degradation by DPP-IV.

Resistance of a peptide to degradation by dipeptidyl aminopeptidase IV is determined by the following degradation assay:

Aliquots of the peptide (5 nmol) are incubated at 37° C. with 1 μL of purified dipeptidyl aminopeptidase IV corresponding to an enzymatic activity of 5 mU for 10-180 minutes in 100 μL of 0.1 M triethylamine-HCl buffer, pH 7.4. Enzymatic reactions are terminated by the addition of 5 μL of 10% trifluoroacetic acid, and the peptide degradation products are separated and quantified using HPLC analysis. One method for performing this analysis is: The mixtures are applied onto a Vydac C18 widepore (30 nm pores, 5 μm particles) 250×4.6 mm column and eluted at a flow rate of 1 ml/min with linear stepwise gradients of acetonitrile in 0.1% trifluoroacetic acid (0% acetonitrile for 3 min, 0-24% acetonitrile for 17 min, 24-48% acetonitrile for 1 min) according to Siegel et al., Regul. Pept. 1999; 79:93-102 and Mentlein et al. Eur. J. Biochem. 1993; 214:829-35. Peptides and their degradation products may be monitored by their absorbance at 220 nm (peptide bonds) or 280 nm (aromatic amino acids), and are quantified by integration of their peak areas related to those of standards. The rate of hydrolysis of a peptide by dipeptidyl aminopeptidase IV is estimated at incubation times which result in less than 10% of the peptide being hydrolysed.

The term "halogen" means F, Cl, Br or I.

The term "$C_{1-6}$alkyl" as used herein means a saturated, branched, straight or cyclic hydrocarbon group having from 1 to 6 carbon atoms. Representative examples include, but are not limited to, methyl, ethyl, n-propyl, isopropyl, butyl, isobutyl, sec-butyl, tert-butyl, n-pentyl, isopentyl, neopentyl, tert-pentyl, n-hexyl, isohexyl, cyclohexyl and the like.

The term "$C_{1-6}$-alkoxy" as used herein is intended to mean a group —O—$C_{1-6}$-alkyl wherein $C_{1-6}$alkyl is as defined above. Representative examples include, but are not limited to, methoxy, ethoxy, n-propoxy, isopropoxy, butoxy, isobutoxy, sec-butoxy, tert-butoxy, n-pentoxy, isopentoxy, neopentoxy, tert-pentoxy, n-hexoxy, isohexoxy, cyclohexoxy and the like.

The term "$C_{1-30}$-alkyl" as used herein means saturated, branched, straight or cyclic hydrocarbon group having from 1 to 30 carbon atoms. Non-limiting examples include ethyl, octyl, hexadecyl, 7-ethylhexadecyl, cyclopentanophenanthrenyl and the like.

The term "$C_{1-30}$-perfluoroalkyl" as used herein means saturated, branched, straight or cyclic hydrocarbon group having from 1 to 30 carbon atoms where all hydrogen atoms have been replaced by fluorine atoms. Non-limiting examples include trifluoromethyl, pentafluoroethyl, heptafluoropropyl, nonafluorobutyl, perfluoroisoamyl, or perfluorocyclohexyl The term "aryl" as used herein is intended to include carbocyclic aromatic ring systems such as phenyl, biphenylyl, naphthyl, anthracenyl, phenanthrenyl, fluorenyl, indenyl, pentalenyl, azulenyl and the like. Aryl is also intended to include the partially hydrogenated derivatives of the carbocyclic systems enumerated above. Non-limiting examples of such partially hydrogenated derivatives are 1,2,3,4-tetrahydronaphthyl, 1,4-dihydronaphthyl and the like.

The term "arylene" as used herein is intended to include arene-derived diradicals such as 1,2-phenylene, 1,3-phenylene, 1,4-phenylene, 1,2-naphthylene, 1,4-naphthylene, and the like.

The term "heteroarylene" as used herein is intended to include heteroarene-derived diradicals, such as 1,2,4-pyrazol-2,5-diyl, imidazol-1,2-diyl, thiazol-2,4-diyl, and the like.

The term "aryloxy" as used herein refers to the radical —O-aryl where aryl is as defined above. Non-limiting examples are phenoxy, naphthoxy, anthracenyloxy, phenantrenyloxy, fluorenyloxy, indenyloxy and the like.

The term "heteroaryl" as used herein is intended to include heterocyclic aromatic ring systems containing one or more heteroatoms selected from nitrogen, oxygen and sulfur such as furyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, indazolyl, benzimidazolyl, benzthiazolyl, benzisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like. Heteroaryl is also intended to include the partially hydrogenated derivatives of the heterocyclic systems enumerated above. Non-limiting examples of such partially hydrogenated derivatives are 2,3-dihydrobenzofuranyl, pyrrolinyl, pyrazolinyl, indanyl, indolinyl, oxazolidinyl, oxazolinyl, oxazepinyl and the like.

Certain of the above defined terms may occur more than once in the structural formulae, and upon such occurrence each term shall be defined independently of the other.

The term "optionally substituted" as used herein means that the groups in question are either unsubstituted or substituted with one or more of the substituents specified. When the groups in question are substituted with more than one substituent the substituents may be the same or different.

DETAILED DESCRIPTION OF THE INVENTION

In one aspect the present invention relates to a method of increasing the intravascular half-life of an agent, characterised by converting said agent into a compound of the general formula (I):

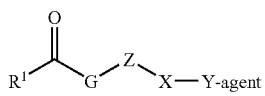

(I)

wherein $R^1$ is the radical of carboxylic acid $R^1$—$CO_2H$, which $R^1$—$CO_2H$ can bind reversibly to a plasma protein, G is NH or CHW, wherein W is hydrogen, fluorine, cyano, nitro, C(=O)-$E^1$, S(=O)$_2$-$E^2$, S(=O)-$E^3$, aryl, or $C_{1-6}$-alkyl, wherein $E^1$, $E^2$, and $E^3$ independently represent $C_{1-6}$-alkyl, aryl, heteroaryl, $C_{1-6}$-alkoxy, amino, $C_{1-6}$alkyl-amino, or di-$C_{1-6}$-alkyl-amino, Z is S=O, S(=O)$_2$, C(=O), C(=O)O, C(=O)N$R^2$, or arylene which is optionally substituted with $C_{1-6}$-alkyl, halogen, nitro, cyano, or heteroarylene, said heteroarylene optionally substituted with $C_{1-6}$-alkyl, halogen, nitro, or cyano, wherein $R^2$ represents hydrogen, cyano, or $C_{1-6}$-alkyl, X represents a bond or a spacer, optionally selected from $C_1$-$C_{20}$-alkylene, arylene, heteroarylene, $C_1$-$C_{20}$-perfluoroalkylene, or combinations thereof, or -[(CQ$_2$)$_n$A]$_m$(CQ$_2$)$_p$-, or -[(CQ$_2$)$_n$A]$_m$(CQ$_2$)$_p$-[(CQ$_2$)$_n$E]$_m$(CQ$_2$)$_p$-, wherein n and m independently are 1-20 and p independently is 0-10, each A and E independently are —O—, —S—, —N$R^3$—, —N(COR$^4$)—, —PR$^5$(O)—, -or P(OR$^6$)(O)—, wherein $R^3$, $R^4$, $R^5$, and $R^6$ independently represent hydrogen or $C_{1-6}$-alkyl, each Q is independently hydrogen or fluorine, Y represents a functional group capable of serving as linker to the agent, optionally selected from —C(=O)—, —C(=S)—, —NR$^7$(C=O)—, —OC(=O)—, —NR$^8$(C=S)—, —CH$_2$—, —CH(OH)—, —S(=O)$_2$—, —NR$^9$—S(=O)$_2$—, —S—, —S—S—, wherein $R^7$, $R^8$, and $R^6$ independently represent hydrogen or $C_{1-6}$-alkyl, and the term 'agent' refers to the compound of which a prolonged half-life in plasma is desired.

In another aspect the present invention the relates to a method of increasing intravascular half-live of a therapeutic agent, characterised by converting said therapeutic agent into a compound of the general formula (II):

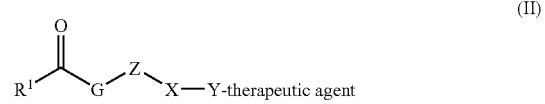

(II)

wherein $R^1$, G, Z, X, and Y are defined as described above.

In one embodiment the present invention relates to a method wherein said therapeutic agent is a biopolymer.

In another embodiment the present invention relates to a method wherein said therapeutic agent is a polypeptide.

In another embodiment the present invention relates to a method wherein the therapeutic agent is a small molecule drug, such as a drug having a molecular weight of less than 1500 Da.

In one aspect the present invention relates to a method for preparation of a compound according to formula (I) or (II), comprising reacting the agent or therapeutic agent with a compound of the general formula (III)

(III)

In one embodiment of the present invention, $Y^1$ is a functional group capable of undergoing a bond-forming reaction with a compound to yield a compound of the general formula (I), $Y^1$ optionally selected from —C(=O)-L, —C(=S)-L, —NR$^2$(C=O)-L, —OC(=O)-L, —NR$^2$(C=S)-L, —C(H$_2$)-L, —C(C$_{1-6}$-alkyl)(=O), —CH(=O), —S(=O)$_2$-L, NR$^2$—S(=O)$_2$-L, —SH, —S-L, —NCO, —NCS, —NCNR$^2$, —NC, —O—NH$_2$ wherein L is a leaving group for nucleophilic displacement, optionally selected from hydroxy, halide, 2,6-dichlorobenzoyl, pivaloyl, 2- or 4-nitrophenyloxy, 2,4-dinitrophenloxy, benzotriazole-1-yloxy, 4-benzotriazol-3-yloxy, $C_{1-6}$-alkoxycarbonyloxy, 4-oxo-3,4-dihydro-1,2,3-benzotriazin-3-yloxy, perfluorophenyloxy, imidazolyl, 2,5-dioxopyrrolidin-1-yloxy, 1,3-dioxo-2,3-dihydro-1-H-isondol-2-yloxy, 2,4,6-trichlorophenyloxy, or azide, and wherein $R^2$ represents hydrogen, cyano, or $C_{1-6}$alkyl.

In another aspect the present invention relates to a compound of the general formula (III):

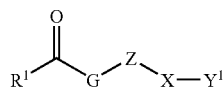
(III)

wherein $R^1$, G, Z, X and $Y^1$ are as defined above.

In another aspect the present invention relates to a compound according to any one of formulae I, II or III, wherein the corresponding acid $R^1$—$CO_2H$ has a binding affinity constant towards human serum albumin that is below about 10 μM or below about 1 μM.

In one embodiment of the present invention, $R^1$ is selected from $C_{1-30}$-alkyl, optionally substituted with one or more —$CO_2H$, —$SO_3H$, —$PO_2OH$, —$SO_2NH_2$, —$NH_2$, —OH, —SH, halogen, or aryl, said aryl optionally substituted with —$CO_2H$, —$SO_3H$, —$PO_2OH$, —$SO_2NH_2$, —$NH_2$, —OH, —SH, or halogen, or $C_{1-30}$-perfluoroalkyl, optionally substituted with one or more —$CO_2H$, —$SO_3H$, —$PO_2OH$, —$SO_2NH_2$, —$NH_2$, —OH, —SH, halogen, or aryl, said aryl optionally substituted with —$CO_2H$, —$SO_3H$, —$PO_2OH$, —$SO_2NH_2$, —$NH_2$, —OH, —SH, or halogen.

In another embodiment of the present invention, $R^1$ is selected from a straight chain alkyl group, a branched alkyl group, a group which has an ω-carboxylic acid group, a partially or completely hydrogenated cyclopentanophenanthrene skeleton.

In another embodiment of the present invention, $R^1$—$CO_2H$ is selected from arylacetic acids, iophenoxate or dicarboxilic acids.

In yet another embodiment of the present invention, $R^1$—$CO_2H$ is ketoprofen or 3-carboxy-4-methyl-5-propyl-2-furanpropionic acid (CMPF).

In yet another embodiment, $R^1$ has from 6 to 40 carbon atoms, from 8 to 26 carbon atoms or from 8 to 20 carbon atoms.

In yet another embodiment, $R^1$ is a peptide, such as a peptide comprising less than 40 amino acid residues. A number of small peptides binding reversibly to human serum albumin are known in the art, see e.g. Dennis M. S. et al. J. Biol. Chem. 277(38), 2002, 35035-35043).

In another embodiment of the present invention, G is NH.

In another embodiment of the present invention, Z is $S(=O)_2$.

In yet another embodiment, Q is H.

In yet another embodiment of the present invention, A and E are both —O—.

In yet another embodiment of the invention, n is 2.

In yet another embodiment the present invention relates to a compound according to any one of formulae I, II, or III, wherein X is a spacer which has a molecular weight in the range from about 80 Da to about 1000 Da, or in the range from about 80 Da to about 300 Da.

In yet another embodiment of the present invention, the therapeutic agent is a biopolymer.

In yet another embodiment of the present invention, the therapeutic agent is a polypeptide.

In yet another embodiment of the present invention, the therapeutic agent is a polypeptide which is attached to Y via a ε-amino group of a lysine residue in said polypeptide.

In yet another embodiment of the present invention, the therapeutic agent is a polypeptide which is attached to Y via an amino acid residue selected from cysteine, glutamate and aspartate.

In one embodiment of the present invention, the therapeutic agent is a GLP-1 peptide.

In another embodiment of the present invention, the therapeutic agent is a GLP-1 peptide selected from GLP-1(7-35), GLP-1 (7-36), GLP-1 (7-36)-amide, GLP-1(7-37), GLP-1(7-38), GLP-1(7-39), GLP-1(7-40), GLP-1(7-41) or an analogue thereof.

In another embodiment of the present invention, the therapeutic agent is a GLP-1 peptide comprising no more than fifteen amino acid residues which have been exchanged, added or deleted as compared to GLP-1(7-37) (SEQ ID No. 1), or no more than ten amino acid residues which have been exchanged, added or deleted as compared to GLP-1 (7-37) (SEQ ID No. 1).

In another embodiment of the present invention, the therapeutic agent is a GLP-1 peptide comprising no more than six amino acid residues which have been exchanged, added or deleted as compared to GLP-1 (7-37) (SEQ ID No. 1).

In another embodiment of the present invention, the therapeutic agent is a GLP-1 peptide comprising no more than 4 amino acid residues which are not encoded by the genetic code.

In another embodiment of the present invention, the therapeutic agent is a GLP-1 peptide which is a DPPIV protected GLP-1 peptide.

In another embodiment of the present invention, the therapeutic agent is a GLP-1 peptide comprising an Aib residue in position 8.

In another embodiment of the present invention, the therapeutic agent is a GLP-1 peptide wherein the amino acid residue in position 7 of said GLP-1 compound is selected from the group consisting of D-histidine, desamino-histidine, 2-amino-histidine, β-hydroxy-histidine, homohistidine, $N^α$-acetyl-histidine, α-fluoromethyl-histidine, and α-methyl-histidine.

In another embodiment of the present invention, the therapeutic agent is a GLP-1 peptide comprising the amino acid sequence of the formula IV:

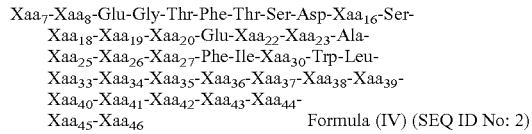

Formula (IV) (SEQ ID No: 2)

wherein $Xaa_7$ is L-histidine, D-histidine, desamino-histidine, 2-amino-histidine, β-hydroxy-histidine, homohistidine, $N^α$-acetyl-histidine, α-fluoromethyl-histidine, α-methyl-histidine, 3-pyridylalanine, 2-pyridylalanine or 4-pyridylalanine;

$Xaa_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
$Xaa_{16}$ is Val or Leu;
$Xaa_{18}$ is Ser, Lys or Arg;
$Xaa_{19}$ is Tyr or Gln;
$Xaa_{20}$ is Leu or Met;
$Xaa_{22}$ is Gly, Glu or Aib;
$Xaa_{23}$ is Gln, Glu, Lys or Arg;
$Xaa_{25}$ is Ala or Val;
$Xaa_{26}$ is Lys, Glu or Arg;
$Xaa_{27}$ is Glu or Leu;
$Xaa_{30}$ is Ala, Glu or Arg;
$Xaa_{33}$ is Val or Lys;
$Xaa_{34}$ is Lys, Glu, Asn or Arg;
$Xaa_{35}$ is Gly or Aib;
$Xaa_{36}$ is Arg, Gly or Lys;
$Xaa_{37}$ is Gly, Ala, Glu, Pro, Lys, amide or is absent;
$Xaa_{38}$ is Lys, Ser, amide or is absent.
$Xaa_{39}$ is Ser, Lys, amide or is absent;
$Xaa_{40}$ is Gly, amide or is absent;
$Xaa_{41}$ is Ala, amide or is absent;
$Xaa_{42}$ is Pro, amide or is absent;
$Xaa_{43}$ is Pro, amide or is absent;
$Xaa_{44}$ is Pro, amide or is absent;
$Xaa_{45}$ is Ser, amide or is absent;
$Xaa_{46}$ is amide or is absent;

provided that if $Xaa_{38}$, $Xaa_{39}$, $Xaa_{40}$, $Xaa_{41}$, $Xaa_{42}$, $Xaa_{43}$, $Xaa_{44}$, $Xaa_{45}$ or $Xaa_{46}$ is absent then each amino acid residue downstream is also absent.

In another embodiment of the present invention, the therapeutic agent is a GLP-1 peptide comprising the amino acid sequence of formula V:

$Xaa_7$-$Xaa_8$-Glu-Gly-Thr-Phe-Thr-Ser-Asp-Val-Ser-$Xaa_{18}$-Tyr-Leu-Glu-$Xaa_{22}$-$Xaa_{23}$-Ala-Ala-$Xaa_{26}$-Glu-Phe-Ile-$Xaa_{30}$-Trp-Leu-Val-$Xaa_{34}$-$Xaa_{35}$-$Xaa_{36}$-$Xaa_{37}$-$Xaa_{38}$   Formula (V) (SEQ ID No: 3)

wherein
$Xaa_7$ is L-histidine, D-histidine, desamino-histidine, 2-amino-histidine, β-hydroxy-histidine, homohistidine, $N^\alpha$-acetyl-histidine, α-fluoromethyl-histidine, α-methyl-histidine, 3-pyridylalanine, 2-pyridylalanine or 4-pyridylalanine;
$Xaa_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;
$Xaa_{18}$ is Ser, Lys or Arg;
$Xaa_{22}$ is Gly, Glu or Aib;
$Xaa_{23}$ is Gln, Glu, Lys or Arg;
$Xaa_{26}$ is Lys, Glu or Arg;
$Xaa_{30}$ is Ala, Glu or Arg;
$Xaa_{34}$ is Lys, Glu or Arg;
$Xaa_{35}$ is Gly or Aib;
$Xaa_{36}$ is Arg or Lys;
$Xaa_{37}$ is Gly, Ala, Glu or Lys;
$Xaa_{38}$ is Lys, amide or is absent.

In another embodiment of the present invention, the therapeutic agent is a GLP-1 peptide selected from the group consisting of $Arg^{34}$GLP-1(7-37), $Lys^{38}Arg^{26,34}$GLP-1(7-38), $Lys^{38}Arg^{26,34}$GLP-1(7-38)-OH, $Lys^{36}Arg^{26,34}$GLP-1 (7-36), $Aib^{8,22,35}$ GLP-1 (7-37), $Aib^{8,35}$ GLP-1(7-37), $Aib^{8,22}$ GLP-1(7-37), $Aib^{8,22,35}$ $Arg^{26,34}Lys^{38}$GLP-1(7-38), $Aib^{8,35}$ $Arg^{26,34}Lys^{38}$GLP-1 (7-38), $Aib^{8,22}$ $Arg^{26,34}Lys^{38}$GLP-1(7-38), $Aib^{8,22,35}$ $Arg^{26,34}Lys^{38}$GLP-1(7-38), $Aib^{8,35}$ $Arg^{26,34}$ $Lys^{38}$GLP-1(7-38), $Aib^{8,22,35}$ $Arg^{26}Lys^{38}$GLP-1(7-38), $Aib^{8,35}$ $Arg^{26}Lys^{38}$GLP-1(7-38), $Aib^{8,22}$ $Arg^{26}Lys^{38}$GLP-1 (7-38), $Aib^{8,22,35}$ $Arg^{34}Lys^{38}$GLP-1(7-38), $Aib^{8,35}$ $Arg^{34}Lys^{38}$GLP-1(7-38), $Aib^{8,22}Arg^{34}Lys^{38}$GLP-1 (7-38), $Aib^{8,22,35}Ala^{37}Lys^{38}$GLP-1(7-38), $Aib^{8,35}Ala^{37}Lys^{38}$GLP-1 (7-38), $Aib^{8,22}Ala^{37}Lys^{38}$GLP-1(7-38), $Aib^{8,22,35}Lys^{37}$GLP-1(7-37), $Aib^{8,35}Lys^{37}$GLP-1(7-37) and $Aib^{8,22}Lys^{37}$GLP-1(7-38).

In another embodiment of the present invention, the therapeutic agent is a GLP-1 peptide which is attached to Y via the amino acid residue in position 23, 26, 34, 36 or 38 relative to the amino acid sequence SEQ ID No:1.

In another embodiment of the present invention, the therapeutic agent is a GLP-1 peptide which is exendin-4 (SEQ-ID No:4).

In another embodiment of the present invention, the therapeutic agent is a GLP-1 peptide which is ZP-10, i.e. HGEGTFTSDLSKQMEEEAVRLFIEWLKNGGPSS-GAPPSKKKKKK-amide (SEQ ID No:5).

In another embodiment of the present invention, the therapeutic agent is a GLP-1 peptide wherein $R^1$—C(=O)-G-Z-X—Y— is attached to said GLP-1 peptide on the C-terminal amino acid residue of said GLP-1 peptide.

In another embodiment of the present invention, the therapeutic agent is a GLP-1 peptide wherein a second $R^1$—C(=O)-G-Z-X—Y— moiety is attached to an amino acid residue which is not the C-terminal amino acid residue.

In another embodiment of the present invention, the therapeutic agent is a GLP-2 peptide.

In another embodiment of the present invention, the therapeutic agent is a GLP-2 peptide which is a DPPIV-protected GLP-2 peptide.

In another embodiment of the present invention, the therapeutic agent is a GLP-2 peptide which is $Gly^2$-GLP-2(1-33).

In another embodiment of the present invention, the therapeutic agent is a GLP-2 peptide which is $Lys^{17}Arg^{30}$-GLP-2 (1-33).

In another embodiment of the present invention, the compound according to formula I or III is $N^{\epsilon 17}$-(6-((2-(3-(Benzoyl)phenyl)propionylamino)sulfonyl)hexanoyl)[$Lys^{17}$, $Arg^{30}$]GLP-2(1-33) or $N^{\delta 17}$-(lauroylsulfamoyl)benzyl-[$Glu^3$,$Gln^{17}$]GLP-2(1-33).

In another embodiment of the present invention, the therapeutic polypeptide is human insulin or an analogue thereof.

In another embodiment of the present invention, the therapeutic polypeptide is selected from the group consisting of is $Asp^{B28}$-human insulin, $Lys^{B28}$, $Pro^{B29}$-human insulin, $Lys^{B3}$, $Glu^{B29}$-human insulin, $Gly^{A21}$,$Arg^{B31}$,$Arg^{B32}$-human insulin and des(B30) human insulin.

In another embodiment of the present invention, the therapeutic polypeptide is human growth hormone or an analogue thereof.

In another embodiment of the present invention, the therapeutic polypeptide is parathyroid hormone or an analogue thereof.

In another embodiment of the present invention, the therapeutic polypeptide is human follicle stimulating hormone or an analogue thereof.

In another embodiment of the present invention, the therapeutic polypeptide has a molar weight of less than 100 kDa, less than 50 kDa, or less than 10 kDa.

In another embodiment of the present invention, the therapeutic polypeptide is selected from the group consisting of a growth factor such as platelet-derived growth factor (PDGF), transforming growth factor α (TGF-α), transforming growth factor β (TGF-β), epidermal growth factor (EGF), vascular endothelial growth factor (VEGF), a somatomedin such as insulin growth factor I (IGF-I), insulin growth factor II (IFG-II), erythropoietin (EPO), thrombopoietin (TPO) or angiopoietin, interferon, pro-urokinase, urokinase, tissue plasminogen activator (t-PA), plasminogen activator inhibitor 1, plasminogen activator inhibitor 2, von Willebrandt factor, a cytokine, e.g. an interleukin such as interleukin (IL) 1, IL-1 Ra, IL-2, IL-4, IL-5, IL-6, IL-9, IL-11, IL-12, IL-13, IL-15, IL-16, IL-17, IL-18, IL-20 or IL-21, a colony stimulating factor (CFS) such as GM-CSF, stem cell factor, a tumor necrosis factor such as TNF-α, lymphotoxin-α, lymphotoxin-β, CD40L, or CD30L, a protease inhibitor e.g. aprotinin, an enzyme such as superoxide dismutase, asparaginase, arginase, arginine deaminase, adenosine deaminase, ribonuclease, catalase, uricase, bilirubin oxidase, trypsin, papain, alkaline phosphatase, β-glucoronidase, purine nucleoside phosphorylase or batroxobin, an opioid, e.g. endorphins, enkephalins or non-natural opioids, a hormone or neuropeptide, e.g. calcitonin, glucagon, gastrins, adrenocorticotropic hormone (ACTH), cholecystokinins, luteinizing hormone, gonadotropin-releasing hormone, chorionic gonadotropin, corticotrophin-releasing factor, vasopressin, oxytocin, antidiuretic hormones, thyroid-stimulating hormone, thyrotropin-releasing hormone, relaxin, prolactin, peptide YY, neuropeptide Y, pancreastic polypeptide, leptin, CART (cocaine and amphetamine regulated transcript), a CART related peptide, perilipin, melanocortins (melanocyte-stimulating hormones) such as α-MSH, melanin-concentrating hormones, natriuretic peptides, adrenomedullin, endothelin, secretin, amylin, vasoactive intestinal peptide (VIP), pituary adenylate cyclase activating polypeptide (PACAP), bombesin, bombesin-like peptides, thymosin, heparin-binding protein, soluble CD4, hypothalmic releasing factor, melanotonins and analogues thereof.

The therapeutic polypeptides can be produced by classical peptide synthesis, e.g. solid phase peptide synthesis using t-Boc or F-Moc chemistry or other well established techniques, see e.g. Green and Wuts, "Protecting Groups in Organic Synthesis", John Wiley & Sons, 1999.

The therapeutic polypeptides can also be produced by a method which comprises culturing a host cell containing a DNA sequence encoding the polypeptide and capable of expressing the polypeptide in a suitable nutrient medium under conditions permitting the expression of the peptide, after which the resulting peptide is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The peptide produced by the cells may then be recovered from the culture medium by conventional procedures including separating the host cells from the medium by centrifugation or filtration. For extracellular products the proteinaceous components of the supernatant are isolated by filtration, column chromatography or precipitation, e.g. microfiltration, ultrafiltration, isoelectric precipitation, purification by a variety of chromatographic procedures, e.g. ion exchange chromatography, hydrophobic interaction chromatography, gel filtration chromatography, affinity chromatography, or the like, dependent on the type of polypeptide in question. For intracellular or periplasmic products the cells isolated from the culture medium are disintegrated or permeabilised and extracted to recover the product polypeptide or precursor thereof.

The DNA sequence encoding the therapeutic polypeptide may suitably be of genomic or cDNA origin, for instance obtained by preparing a genomic or cDNA library and screening for DNA sequences coding for all or part of the peptide by hybridisation using synthetic oligonucleotide probes in accordance with standard techniques (see, for example, Sambrook, J, Fritsch, E F and Maniatis, T, Molecular Cloning: A Laboratory Manual, Cold Spring Harbor Laboratory Press, New York, 1989). The DNA sequence encoding the polypeptide may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. The DNA sequence may also be prepared by polymerase chain reaction using specific primers, for instance as described in U.S. Pat. No. 4,683,202 or Saiki et al., Science 239 (1988), 487-491.

The DNA sequence may be inserted into any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the polypeptide is operably linked to additional segments required for transcription of the DNA, such as a promoter. The promoter may be any DNA sequence which shows transcriptional activity in the host cell of choice and may be derived from genes encoding proteins either homologous or heterologous to the host cell. Examples of suitable promoters for directing the transcription of the DNA encoding the peptide of the invention in a variety of host cells are well known in the art, cf. for instance Sambrook et al., supra.

The DNA sequence encoding the polypeptide may also, if necessary, be operably connected to a suitable terminator, polyadenylation signals, transcriptional enhancer sequences, and translational enhancer sequences. The recombinant vector of the invention may further comprise a DNA sequence enabling the vector to replicate in the host cell in question.

The vector may also comprise a selectable marker, e.g. a gene the product of which complements a defect in the host cell or one which confers resistance to a drug, e.g. ampicillin, kanamycin, tetracyclin, chloramphenicol, neomycin, hygromycin or methotrexate. For large scale manufacture the selectable marker preferably is not antibiotic resistance, e.g. antibiotic resistance genes in the vector are preferably excised when the vector is used for large scale manufacture. Methods for eliminating antibiotic resistance genes from vectors are known in the art, see e.g. U.S. Pat. No. 6,358,705 which is incorporated herein by reference.

To direct a parent peptide of the present invention into the secretory pathway of the host cells, a secretory signal sequence (also known as a leader sequence, prepro sequence or pre sequence) may be provided in the recombinant vector. The secretory signal sequence is joined to the DNA sequence encoding the peptide in the correct reading frame. Secretory signal sequences are commonly positioned 5' to the DNA sequence encoding the peptide. The secretory signal sequence may be that normally associated with the peptide or may be from a gene encoding another secreted protein.

The procedures used to ligate the DNA sequences coding for the present peptide, the promoter and optionally the terminator and/or secretory signal sequence, respectively, and to insert them into suitable vectors containing the information necessary for replication, are well known to persons skilled in the art (cf., for instance, Sambrook et al., supra).

The host cell into which the DNA sequence or the recombinant vector is introduced may be any cell which is capable of producing the present peptide and includes bacteria, yeast, fungi and higher eukaryotic cells. Examples of suitable host cells well known and used in the art are, without limitation, *E. coli, Saccharomyces cerevisiae*, or mammalian BHK or CHO cell lines.

In another aspect the present invention relates to a compound selected from the group consisting of

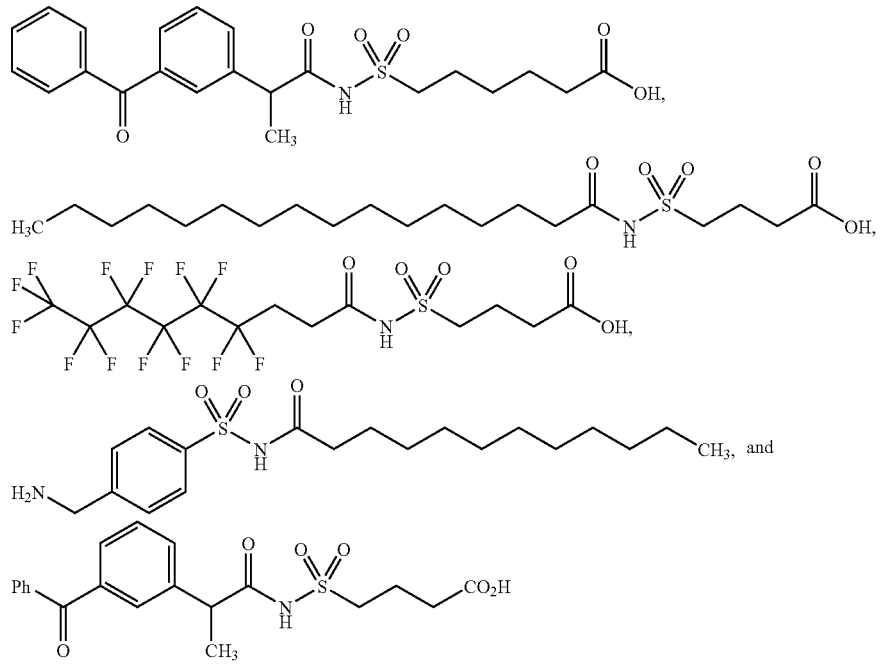

In another aspect the present invention relates to the use of a compound selected from the group consisting of

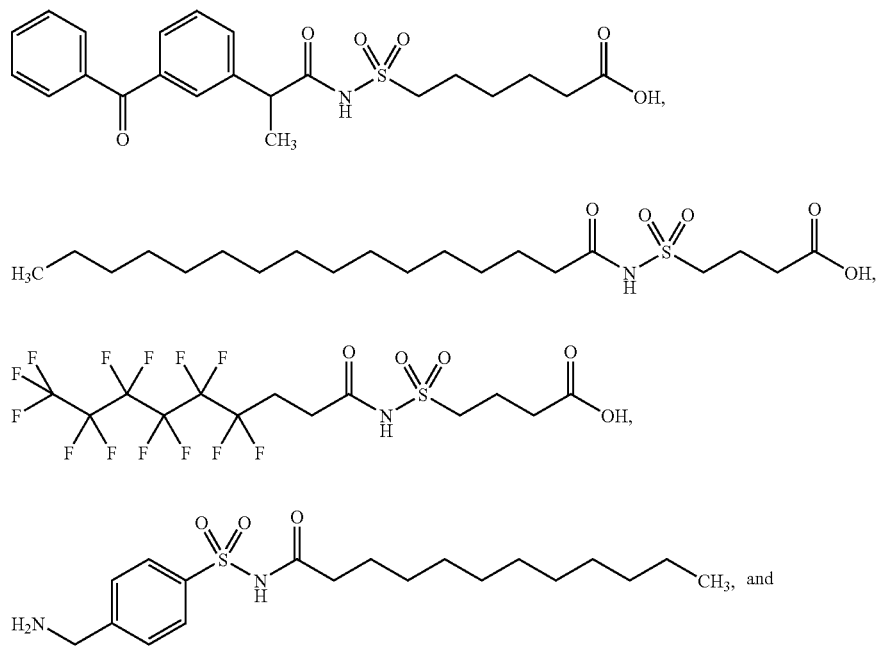

-continued

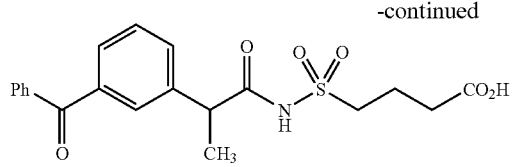

for modifying the pharmacokinetic properties of a therapeutic polypeptide by derivatization of said therapeutic polypeptide with said compound.

Pharmaceutical compositions containing a compound according to the present invention may be prepared by conventional techniques, e.g. as described in Remington's *Pharmaceutical Sciences*, 1985 or in Remington: *The Science and Practice of Pharmacy*, 19$^{th}$ edition, 1995.

One object of the present invention is to provide a pharmaceutical formulation comprising a compound according to the present invention which is present in a concentration from about 0.1 mg/ml to about 25 mg/ml, and wherein said formulation has a pH from 2.0 to 10.0. The formulation may further comprise a buffer system, preservative(s), isotonicity agent(s), chelating agent(s), stabilizers and surfactants. In one embodiment of the invention the pharmaceutical formulation is an aqueous formulation, i.e. formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical formulation is a freeze-dried formulation, whereto the physician or the patient adds solvents and/or diluents prior to use.

In another embodiment the pharmaceutical formulation is a dried formulation (e.g. freeze-dried or spray-dried) ready for use without any prior dissolution.

In a further aspect the invention relates to a pharmaceutical formulation comprising an aqueous solution of a compound according to the present invention, and a buffer, wherein said compound is present in a concentration from 0.1 mg/ml or above, and wherein said formulation has a pH from about 2.0 to about 10.0.

In a further aspect the invention relates to a pharmaceutical formulation comprising an aqueous solution of a compound according to the present invention, and a buffer, wherein said compound is present in a concentration from 0.1 mg/ml or above, and wherein said formulation has a pH from about 7.0 to about 8.5.

In a another embodiment of the invention the pH of the formulation is selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0.

In a further embodiment of the invention the buffer is selected from the group consisting of sodium acetate, sodium carbonate, citrate, glycylglycine, histidine, glycine, lysine, arginin, sodium dihydrogen phosphate, disodium hydrogen phosphate, sodium phosphate, and tris(hydroxymethyl)-aminomethane, bicine, tricine, malic acid, succinate, maleic acid, fumaric acid, tartaric acid, aspartic acid or mixtures thereof. Each one of these specific buffers constitutes an alternative embodiment of the invention.

In a further embodiment of the invention the formulation further comprises a pharmaceutically acceptable preservative. In a further embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy*, 19$^{th}$ edition, 1995.

In a further embodiment of the invention the formulation further comprises an isotonic agent. In a further embodiment of the invention the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one—OH group and includes, for example, mannitol, sorbitol, inositol, galacitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a chelating agent. In a further embodiment of the invention the chelating agent is selected from salts of ethylenediaminetetraacetic acid (EDTA), citric acid, and aspartic acid, and mixtures thereof. In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a stabiliser. The use of a stabilizer in pharmaceutical compositions is well-known to the skilled person. For convenience reference is made to Remington: *The Science and Practice of Pharmacy*, 19$^{th}$ edition, 1995.

More particularly, compositions of the invention are stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. In one embodiment, the amino acid used for preparing the compositions of the invention is glycine. Any stereoisomer (i.e. L or D) of a particular amino acid (e.g. methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include S-ethyl homocysteine and S-butyl homocysteine and suitable cystein analogues include S-methyl-L cystein. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention methionine (or other sulphur containing amino acids or amino acid analogous) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L, D, or a mixture thereof) can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide. Generally, this can be achieved by adding methionine such that the ratio of methionine added to methionine residues ranges from about 1:1 to about 1000:1, such as 10:1 to about 100:1.

In a further embodiment of the invention the formulation further comprises a stabiliser selected from the group of high molecular weight polymers or low molecular compounds. In a further embodiment of the invention the stabilizer is selected from polyethylene glycol (e.g. PEG 3350), polyvinylalcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In a further embodiment of the invention the formulation further comprises a surfactant. In a further embodiment of the invention the surfactant is selected from a detergent, ethoxylated castor oil, polyglycolyzed glycerides, acetylated monoglycerides, sorbitan fatty acid esters, polyoxypropylene-polyoxyethylene block polymers (e.g. poloxamers such as Pluronic® F68, poloxamer 188 and 407, Triton X-100), polyoxyethylene sorbitan fatty acid esters, polyoxyethylene and polyethylene derivatives such as alkylated and alkoxylated derivatives (tweens, e.g. Tween-20, Tween-40, Tween-80 and Brij-35), monoglycerides or ethoxylated derivatives thereof, diglycerides or polyoxyethylene derivatives thereof, alcohols, glycerol, lecitins and phospholipids (e.g. phosphatidyl serine, phosphatidyl choline, phosphatidyl ethanolamine, phosphatidyl inositol, diphosphatidyl glycerol and sphingomyelin), derivates of phospholipids (e.g. dipalmitoyl phosphatidic acid) and lysophospholipids (e.g. palmitoyl lysophosphatidyl-L-serine and 1-acyl-sn-glycero-3-phosphate esters of ethanolamine, choline, serine or threonine) and alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, and glycerophospholipids (e.g. cephalins), glyceroglycolipids (e.g. galactopyransoide), sphingoglycolipids (e.g. ceramides, gangliosides), dodecylphosphocholine, hen egg lysolecithin, fusidic acid derivatives-(e.g. sodium tauro-dihydrofusidate etc.), long-chain fatty acids and salts thereof C6-C12 (e.g. oleic acid and caprylic acid), acylcarnitines and derivatives, $N^{\alpha}$-acylated derivatives of lysine, arginine or histidine, or side-chain acylated derivatives of lysine or arginine, $N^{\alpha}$-acylated derivatives of dipeptides comprising any combination of lysine, arginine or histidine and a neutral or acidic amino acid, $N^{\alpha}$-acylated derivative of a tripeptide comprising any combination of a neutral amino acid and two charged amino acids, DSS (docusate sodium, CAS registry no [577-11-7]), docusate calcium, CAS registry no [128-49-4]), docusate potassium, CAS registry no [7491-09-0]), SDS (sodium dodecyl sulfate or sodium lauryl sulfate), sodium caprylate, cholic acid or derivatives thereof, bile acids and salts thereof and glycine or taurine conjugates, ursodeoxycholic acid, sodium cholate, sodium deoxycholate, sodium taurocholate, sodium glycocholate, N-hexadecyl-N,N-dimethyl-3-ammonio-1-propanesulfonate, anionic (alkyl-aryl-sulphonates) monovalent surfactants, zwitterionic surfactants (e.g. N-alkyl-N,N-dimethylammonio-1-propanesulfonates, 3-cholamido-1-propyldimethylammonio-1-propanesulfonate, cationic surfactants (quarternary ammonium bases) (e.g. cetyl-trimethylammonium bromide, cetylpyridinium chloride), non-ionic surfactants (e.g. dodecyl β-D-glucopyranoside), poloxamines (e.g. Tetronic's), which are tetrafunctional block copolymers derived from sequential addition of propylene oxide and ethylene oxide to ethylenediamine, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: *The Science and Practice of Pharmacy*, 19$^{th}$ edition, 1995.

A composition for parenteral administration of GLP-1 compounds may, for example, be prepared as described in WO 03/002136.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatin or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing a compound according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the compound, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Compositions of the current invention are useful in the formulation of solids, semisolids, powder and solutions for pulmonary administration of the compound, using, for example a metered dose inhaler, dry powder inhaler and a nebulizer, all being devices well known to those skilled in the art.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles, Methods to produce controlled release systems useful for compositions of the current invention include, but are not limited to, crystallization, condensation, co-cystallization, precipitation, co-precipitation, emulsification, dispersion, high pressure homogenization, encapsulation, spray drying, microencapsulation, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000).

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the compound according to the present invention in the form of a nasal or pulmonal spray. As a still further option, the pharmaceutical compositions containing the compound of the invention can also be adapted to transdermal administration, e.g. by needle-free injection or from a patch, optionally an iontophoretic patch, or transmucosal, e.g. buccal, administration.

The term "stabilized formulation" refers to a formulation with increased physical stability, increased chemical stability or increased physical and chemical stability.

The term "physical stability" of the protein formulation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person. Physical stability of the aqueous protein formulations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as anthracene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein formulation as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized formulation" refers to a formulation with increased physical stability, increased chemical stability or increased physical and chemical stability. In general, a formulation must be stable during use and storage (in compliance with recommended use and storage conditions) until the expiration date is reached.

In one embodiment of the invention the pharmaceutical formulation comprising the compound according to the present invention is stable for more than 6 weeks of usage and for more than 3 years of storage.

In another embodiment of the invention the pharmaceutical formulation comprising the compound according to the present invention is stable for more than 4 weeks of usage and for more than 3 years of storage.

In a further embodiment of the invention the pharmaceutical formulation comprising the compound according to the present invention is stable for more than 4 weeks of usage and for more than two years of storage.

In an even further embodiment of the invention the pharmaceutical formulation comprising the compound is stable for more than 2 weeks of usage and for more than two years of storage.

In another aspect the present invention relates to the use of a compound according to the invention for the preparation of a medicament.

In one embodiment of the invention a compound according to the invention wherein the therapeutic agent is a GLP-1 peptide is used for the preparation of a medicament for the treatment or prevention of hyperglycemia, type 2 diabetes, impaired glucose tolerance, type 1 diabetes, obesity, hypertension, syndrome X, dyslipidemia, cognitive disorders, atheroschlerosis, myocardial infarction, coronary heart disease and other cardiovascular disorders, stroke, inflammatory bowel syndrome, dyspepsia and gastric ulcers.

In another embodiment of the invention a compound according to the invention wherein the therapeutic agent is a GLP-1 peptide is used for the preparation of a medicament for delaying or preventing disease progression in type 2 diabetes.

In another embodiment of the invention a compound according to the invention wherein the therapeutic agent is a GLP-1 peptide is used for the preparation of a medicament for decreasing food intake, decreasing β-cell apoptosis, increasing β-cell function and β-cell mass, and/or for restoring glucose sensitivity to β-cells.

In another embodiment the present invention relates to the use of a compound according to the invention wherein the therapeutic agent is a GLP-2 peptide for the preparation of a medicament for the treatment of small bowel syndrome, inflammatory bowel syndrome or Crohns disease.

In another embodiment the present invention relates to the use of a compound according to the invention wherein the therapeutic agent is an insulin peptide for the preparation of a medicament for the treatment of hyperglycemia, type 1 diabetes, type 2 diabetes or β-cell deficiency.

The treatment with a compound according to the present invention may also be combined with combined with a second or more pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, GLP-1 agonists, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists.

It should be understood that any suitable combination of the compounds according to the invention with one or more of the above-mentioned compounds and optionally one or more further pharmacologically active substances are considered to be within the scope of the present invention.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLES

In the examples the following terms are intended to have the following, general meanings:

DBU: 1,8-diazabicyclo[5.4.0]undec-7-ene
DCM: dichloromethane, methylenechloride
DMA: N,N-dimethylacetamide
DMF: N,N-dimethyl formamide
DMSO: dimethyl sulfoxide
EDC: N-ethyl-N'-(3-dimethylaminopropyl)carbodiimide hydrochloride
HOAt: 3-hydroxy-3H-[1,2,3]triazolo[4,5-b]pyridine, 4-aza-3-hydroxybenzotriazole
HOBt: N-hydroxybenzotriazole, 1-hydroxybenzotriazole
NMP: N-methylpyrrolidone NMR spectra were recorded on Bruker 300 MHz and 400 MHz instruments. HPLC-MS was performed on a Perkin Elmer instrument (API 100).

HPLC-systems from Merck-Hitachi (Hibar™ RT 250-4, Lichrosorb™ RP 18, 5.0 μm, 4.0×250 mm, gradient elution, 20% to 80% acetonitrile in water within 30 min, 1.0 ml/min, detection at 254 nm) and Waters (Symmetry™, C18, 3.5 μm, 3.0×150 mm, gradient elution, 5% to 90% acetonitrile in water within 15 min, 1.0 ml/min, detection at 214 nm) were used.

Furthermore, where stated the following HPLC method h8 was used:

The reverse phase analysis was performed using UV detections at 214, 254, 276 and 301 nm on a 218TP54 4.6 mm×150 mm C-18 silica column, which was eluted at 1 ml/min at 42° C. The column was equilibrated with 5% acetonitrile, 85% water and 10% of a solution of 0.5% trifluoroacetic acid in water and eluted by a linear gradient from 5% acetonitrile, 85% water and 10% of a solution of 0.5% trifluoroacetic acid to 90% acetonitrile and 10% of a solution of 0.5% trifluoroacetic acid over 15 min.

Furthermore, where stated the following HPLC method A was used:

The RP-analysis was performed using a Waters 2690 systems fitted with a Waters 996 diode array detector. UV detections were collected at 214, 254, 276, and 301 nm on a 218TP54 4.6 mm×250 mm 5μ C-18 silica column (The Seperations Group, Hesperia), which was eluted at 1 ml/min at 42° C. The column was equilibrated with 5% acetonitrile (+0.1% TFA) in an aqueous solution of TFA in water (0.1%). After injection, the sample was eluted by a gradient of 0% to 90% acetonitrile (+0.1% TFA) in an aqueous solution of TFA in water (0.1%) during 50 min.

General Procedure (A)

The compounds of formula (I) according to the invention may be prepared by the general procedure (A):

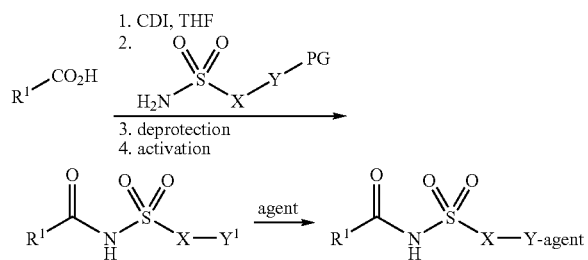

The plasma-protein binding acid is dissolved in a suitable solvent, such as THF, and treated with a slight excess of carbonyl diimidazole. When the formation of the acid imidazolide is completed, a sulfonamide of the general formula $H_2N—S(O)_2—X—Y$-PG (PG=protective group) is added to the reaction mixture, followed by a suitable base, such as DBU. When the reaction is completed, the solvent is evaporated, and the product is purified by extraction and column chromatography.

The resulting intermediate is then deprotected, activated, and then treated with the agent or a partially protected derivative thereof to yield, after final deprotection, the desired substance.

Example 1

6-[2-(3-Benzoylphenyl)propionylsulfamoyl]hexanoic acid

First Step: 6-sulfohexanoic acid ethyl ester

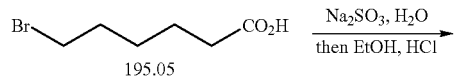

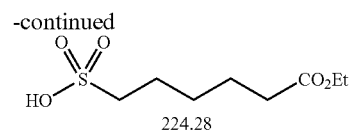

A mixture of 6-bromohexanoic acid (9.75 g, 50.0 mmol), sodium sulfite (25.2 g, 200 mmol), and water (100 ml) was stirred at 100° C. overnight. The mixture was then acidified by addition of concentrated, aqueous hydrochloric acid (35 ml), and concentrated under reduced pressure. To the residue was added ethanol, and the mixture was again concentrated. The residue was resuspended in ethanol, and the salts were removed by filtration. The filtrate was concentrated, and the residue was dried by threefold azeotropic concentration with toluene. 13.4 g (quant.) of the title compound was obtained as an oil.

$^1$H NMR (CDCl$_3$) δ 1.27 (t, J=7 Hz, 3H), 1.50 (m, 2H), 1.68 (m, 2H), 1.87 (m, 2H), 2.36 (m, 2H), 3.12 (t, J=7 Hz, 2H), 4.13 (quart, J=7 Hz, 2H), 10.42 (s, br, 2H).

Second Step: 6-chlorosulfonylhexanoic acid ethyl ester

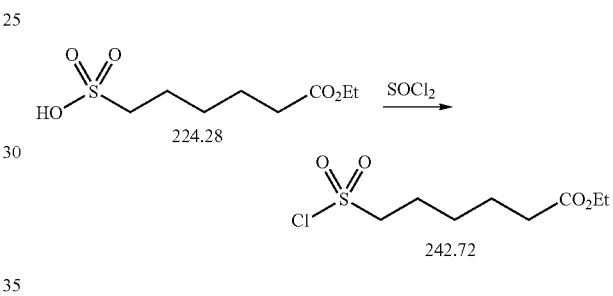

The product of the previous reaction (13.4 g, max 50 mmol) was dissolved in thionyl chloride (50 ml) and heated to reflux overnight. The mixture was concentrated, and the residue coevaporated with toluene three times to yield 13.4 g (quant) of the title compound.

$^1$H NMR (CDCl$_3$) δ 1.26 (t, J=7 Hz, 3H), 1.52 (m, 2H), 1.68 (m, 2H), 1.97 (m, 2H), 2.32 (t, J=7 Hz, 2H), 3.54 (t, J=7 Hz, 2H), 4.13 (quart, J=7 Hz, 2H).

Third Step: 6-sulfamoylhexanoic acid ethyl ester

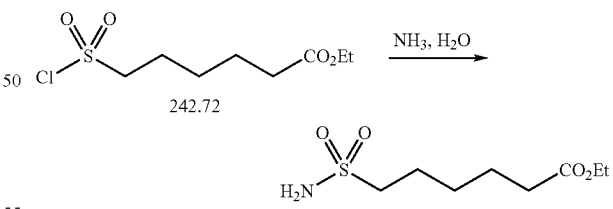

The product of the previous reaction (13.4 g, max 50 mmol) was dissolved in aqueous ammonia (80 ml, 25% NH$_3$) and allowed to stand at room temperature for 10 min. The mixture was concentrated under reduced pressure, and the residue was dried by repeated coevaporation with ethanol. The residue was then distributed between an aqueous saturated NaHCO$_3$ solution and dichloromethane. The dichloromethane phase was washed once with water, dried with MgSO$_4$, and concentrated to yield 2.55 g (23%) of the sulfonamide.

$^1$H NMR (CDCl$_3$) δ 1.26 (t, J=7 Hz, 3H), 1.50 (m, 2H), 1.68 (m, 2H), 1.89 (m, 2H), 2.32 (t, J=7 Hz, 2H), 3.12 (t, J=7 Hz, 2H), 4.12 (quart, J=7 Hz, 2H), 4.55 (br s, 2H).

Fourth Step: 1: 6-[2-(3-benzoylphenyl)propionylsulfamoyl]hexanoic acid ethyl ester

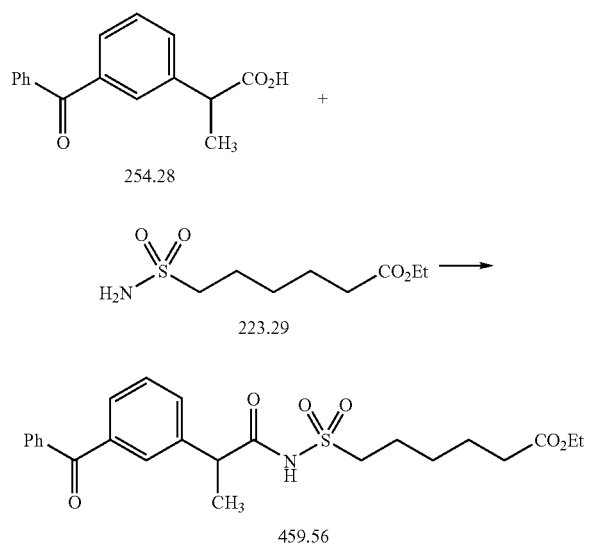

To a suspension of racemic ketoprofen (3.81 g, 15.0 mmol) in dichloromethane (50 ml) were added HOAt (2.04 g, 15.0 mmol) and EDC (2.88 g, 15.0 mmol), and the mixture was stirred until a clear solution resulted. To this solution was added a solution of 6-sulfamoylhexanoic acid ethyl ester (2.23 g, 10.0 mmol) and DI PEA (2.56 ml) in dichloromethane, and the mixture was stirred at room temperature for 3 d. The mixture was washed with 1N aqueous HCl, dried over MgSO$_4$, and concentrated. Purification by column chromatography yielded 2.0 g (44%) of the title compound. An analytical sample was obtained by preparative HPLC.

$^1$H NMR (CDCl$_3$) δ 1.23 (t, J=7 Hz, 3H), 1.39 (m, 2H), 1.52 (d, J=7 Hz, 3H), 1.62 (m, 2H), 2.24 (t, J=7 Hz, 2H), 3.38 (t, J=7 Hz, 2H), 3.79 (quart, J=7 Hz, 1H), 4.09 (quart, J=7 Hz, 2H), 7.45-7.69 (m, 6H), 7.78 (m, 3H), 8.85 (br s, 1H).

Fifth Step: 1: 6-[2-(3-benzoylphenyl)propionylsulfamoyl]hexanoic acid

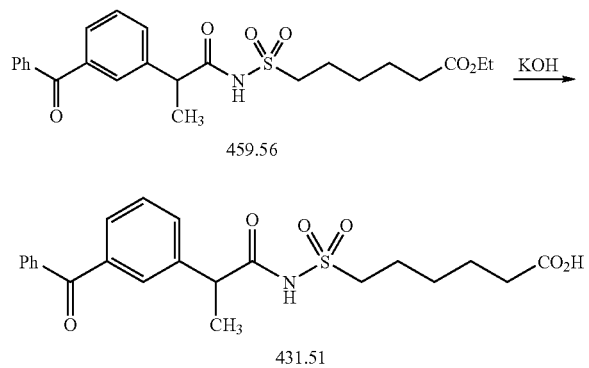

To a solution of the ester (1.0 g, 2.18 mmol) in ethanol (50 ml) was added an aqueous solution of potassium hydroxide (15 ml, 5%), and the mixture was stirred at room temperature overnight. The mixture was concentrated, and the residue acidified by addition of dilute HCl. The product was extracted twice with dichloromethane, and the combined filtrates were dried (MgSO$_4$) and concentrated to yield 0.85 g (91%) of the title acid as an oil.

$^1$H NMR (CDCl$_3$) δ 1.42 (m, 2H), 1.52 (d, J=7 Hz, 3H), 1.62 (m, 2H), 2.29 (t, J=7 Hz, 2H), 3.38 (t, J=7 Hz, 2H), 3.79 (quart, J=7 Hz, 1H), 7.42-7.66 (m, 6H), 7.78 (m, 3H), 9.05 (br s, 1H).

Example 2

GLP-2 Analogue Acylated at Position 17 with the Acylsulfonamide from Example 1:

N$^{ε17}$-(6-((2-(3-(Benzoyl)phenyl)propionylamino)sulfonyl)hexanoyl)[Lys$^{17}$ Arg$^{30}$]GLP-2(1-33)

A resin (loading: 1.05 mmol/g) Fmoc-His(Boc)-Ala-Asp(OtBu)-Gly-Ser(tBu)-Phe-Ser(tBu)-Asp(OtBu)-Glu(OtBu)-Met-Asn(Trt)-Thr(tBu)-Ile-Leu-Asp(OtBu)-Asn(Trt)-Lys(Mtt)-Ala-Ala-Arg(Pmc)-Asp(OtBu)-Phe-Ile-Asn(Trt)-Trp(Boc)-Leu-Ile-Gln(Trt)-Thr(tBu)-Arg(Pmc)-Ile-Thr(tBu)-Asp(OtBu)-O-Wang was prepared after standard peptide-chemistry using a FMOC-protection strategy, which is known to a person skilled in the art and described in e.g. Bodanszky and Bodanzsky, The practice of peptide synthesis Springer Verlag, 2$^{nd}$ edition, Berlin 1994. The resin (approx. 0.1 mmol) was suspended in dichloromethane (20 ml). The solvent was removed. A solution of trifluoroacetic acid (2%) and triisopropylsilane (2%) in dichloromethane (10 ml) was added to the resin. The reaction vessel was shaken for 10 min at room temperature. The liquid was removed. This latter procedure was repeated four times. The resin was washed with N,N-dimethylformamide (3×10 ml) and dichloromethane (3×10 ml). A solution of 6-[2-(3-benzoylphenyl)propionylsulfamoyl]hexanoic acid (0.17 g, 0.4 mmol) in N,N-dimethylformamide (5 ml) was added to the resin. A solution of 1-hydroxybenzotriazole (HOBt, 0.061 g, 0.4 mmol) in N,N-dimethylformamide (5 ml) was added to the resin. A solution of diisopropylcarbodiimide (DIC 0.06 ml, 0.4 mmol) and ethyldiisopropylamine (0.137 ml, 0.8 mmol) in dichloromethane (10 ml) was added to the resin. The reaction vessel was shaken for 16 h at room temperature. The liquid was removed. The resin was washed with N,N-dimethylformamide (3×10 ml) and dichloromethane (3×10 ml). The Fmoc-group was removed with a solution of piperidine (20%) in N,N-dimethylformamide, using a procedure known to a person skilled in the art and described in e.g. Bodanszky and Bodanzsky, The practice of peptide synthesis Springer Verlag, 2$^{nd}$ edition, Berlin 1994. The peptide was removed from the resin using a solution of water (2.5%) and triisopropylsilane (2.5%) in trifluoroacetic acid with a procedure known to a person skilled in the art and described in e.g. Bodanszky and Bodanzsky, The practice of peptide synthesis Springer Verlag, 2$^{nd}$ edition, Berlin 1994.

The compound was purified by reverse-phase HPLC using a gradient of 30-80% of acetonitrile in water in an environment, which was acidic with trifluoroacetic acid (0.1%).

MS: 1408.8 and 1056.9. HPLC: 29.99 min (Method A)

Example 3

6-[2-(3-Benzoylphenyl)propionylsulfamoyl]butanoic acid

First Step: 4-sulfamoylbutyric acid methyl ester

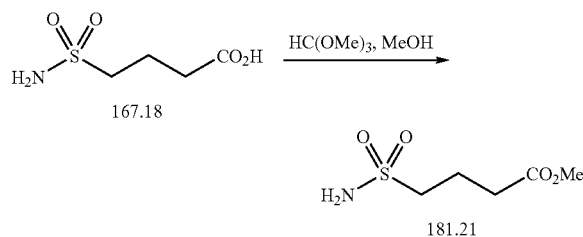

A mixture of 4-sulfamoylbutyric acid (2.53 g, 15.1 mmol), methanol (25 ml), trimethylorthoformate (10 ml, approx 5 eq) and polystyrene-bound toluenesulfonic acid (0.58 g) was stirred at 60° C. After 19 h the mixture was decantated from the catalyst and concentrated to yield 2.70 g (99%) of the title ester as an oil.

$^1$H NMR (DMSO) δ 1.92 (m, 2H), 2.49 (t, J=7 Hz, 2H), 3.00 (m, 2H), 3.60 (s, 3H), 6.82 (br s, 2H).

Second Step: 6-[2-(3-benzoylphenyl)propionylsulfamoyl] butyric acid methyl ester

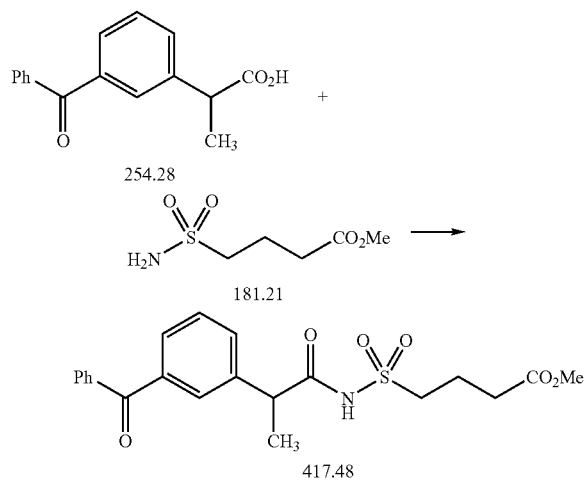

To a solution of ketoprofen (2.66 g, 10.5 mmol) in THF (30 ml) was added carbonyl diimidazole (1.94 g, 12.0 mmol). The solution was stirred at room temperature for 20 h and then at 60° C. for 30 min. Then a solution of 4-sulfamoylbutyric acid methyl ester (1.74 g, 9.60 mmol) in THF (10 ml) was added, followed by the addition of DBU (1.70 ml, 11.4 mmol). The mixture was stirred at 60° C. for 25 h, concentrated, and the residue was mixed with water (100 ml) and 1N HCl (50 ml). The product was extracted twice with ethyl acetate, and the combined extracts were washed with brine and a saturated, aqueous solution of sodium bicarbonate, dried over MgSO$_4$ and concentrated. The residue was purified by column chromatography (45 g silica gel, gradient elution heptane/ethyl acetate) to yield 1.20 g (30%) of the title compound as an oil.

$^1$H NMR (DMSO) δ 1.39 (d, J=7 Hz, 3H), 1.78 (m, 2H), 2.39 (t, J=7 Hz, 2H), 3.38 (t, J=7 Hz, 2H), 3.55 (s, 3H), 3.87 (quart, J=7 Hz, 1H), 7.51-7.78 (m, 9H), 11.91 (br s, 1H).

Third Step: 6-[2-(3-benzoylphenyl)propionylsulfamoyl]butyric

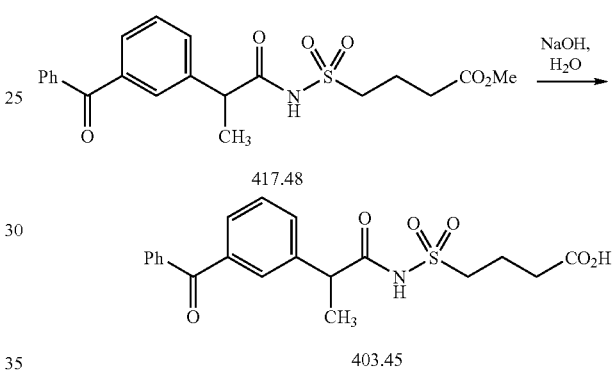

To a solution of 6-[2-(3-benzoylphenyl)propionylsulfamoyl]butyric acid methyl ester (0.73 g, 1.75 mmol) in methanol (5 ml) was added a solution of sodium hydroxide (0.40 g, 10 mmol) in water (1.0 ml). The mixture was stirred at room temperature for 2 h. 1N Hydrochloric acid (10 ml) and water (50 ml) were added, and the product was extracted three times with ethyl acetate. The combined extracts were washed with brine, dried over MgSO4, and concentrated, to yield 0.65 g (92%) of the title compound as a foam.

$^1$H NMR (DMSO) δ 1.39 (d, J=7 Hz, 3H), 1.78 (m, 2H), 2.33 (t, J=7 Hz, 2H), 3.38 (t, J=7 Hz, 2H), 3.86 (quart, J=7 Hz, 1H), 7.51-7.76 (m, 9H), 11.89 (br s, 1H), 12.21 (br s, 1H).

Example 4

4-(Palmitoylsulfamoyl)butyric acid

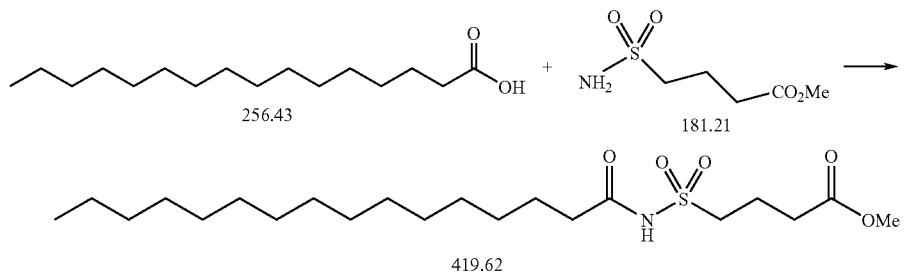

Step 1:

To a suspension of palmitic acid (1.67 g, 6.51 mmol) in toluene (6.0 ml) was added oxalyl chloride (0.56 ml, 6.53 mmol). After 45 min the resulting clear solution was added to a flask containing 4-sulfamoylbutyric acid methyl ester (0.91 g, 5.02 mmol), and the mixture was diluted with DCM (5.0 ml). To this mixture was added DMAP (1.90 g, 15.5 mmol) in small portions. The mixture was stirred at room temperature for 19 h. A mixture of water (100 ml) and 1N HCl (20 ml) was added, followed by extraction with AcOEt/DCM, washing of the combined extracts with brine, drying (MgSO4), and concentration under reduced pressure. The resulting solid (2.26 g) was recrystallized from hot AcOEt (approx 10 ml), to yield 1.59 g (76%) of the methyl ester as almost colorless solid, mp: 100-103° C.

$^1$H NMR (DMSO-$d_6$): δ 0.84 (m, 3H), 1.23 (br s, 24H), 1.49 (m, 2H), 1.88 (m, 2H), 2.24 (t, J=7 Hz, 2H), 2.49 (t, J=7 Hz, 2H), 3.38 (m, 2H), 3.59 (s, 3H), 11.58 (s, 1H).

Step 2: Saponification:

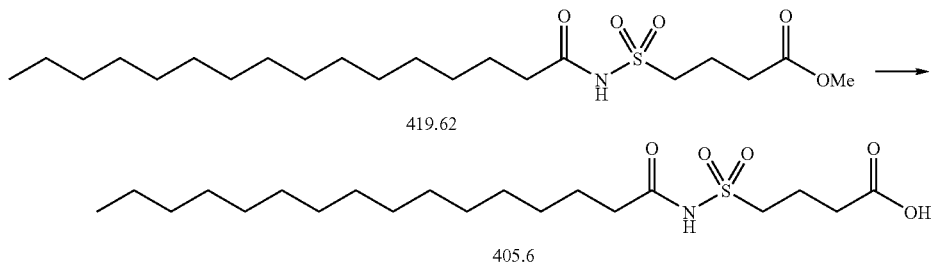

To a suspension of the methyl ester (0.84 g, 2.00 mmol) in methanol (10 ml) was added a solution of NaOH (0.54 g, 13.5 mmol) in water (1.0 ml). The mixture was stirred at room temperature for 4 h. A mixture of water (30 ml) and 1N HCl (20 ml) was added, and the product was isolated by filtration. Recrystallization from boiling MeCN (50 ml) yielded 0.64 g (79%) of the title compound as colorless plates. M.p.: 156-157° C.

$^1$H NMR (DMSO-$d_6$): δ 0.85 (m, 3H), 1.23 (br s, 24H), 1.49 (m, 2H), 1.85 (m, 2H), 2.25 (t, J=7 Hz, 2H), 2.39 (t, J=7 Hz, 2H), 11.15 (s, 1H).

Example 5

4-(4,4,5,5,6,6,7,7,8,8,9,9,9-Tridecafluorononanoyl-sulfamoyl)butyric acid

Step 1:

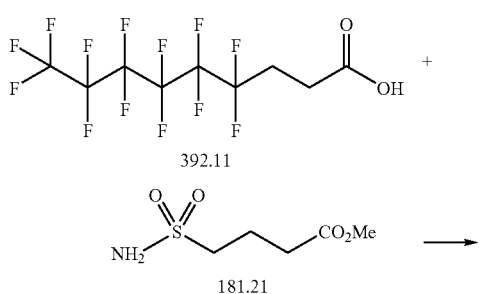

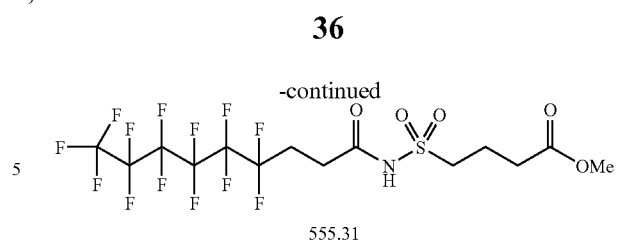

4,4,5,5,6,6,7,7,8,8,9,9,9-Tridecafluorononanoic acid (3.07 g, 7.83 mmol) was mixed with thionyl chloride (20 ml) and stirred at 80° C. for 1.5 h. The mixture was concentrated and the residue stripped once with toluene. The residual liquid was dissolved in DCM (5 ml) and this solution was added to a solution of 4-sulfamoylbutyric acid methyl ester (1.15 g, 6.35 mmol) in DCM (5 ml). To this mixture DMAP (2.34 g, 19.3 mmol) was added in small portions while stirring energetically. During the addition the mixture became viscous, and more DCM (10 ml) was added. The resulting mixture was stirred at room temperature for 66 h, whereby it turned black. A mixture of water (100 ml) and 1N HCl (30 ml) was added, and the product was extracted (3× AcOEt; emulgates strongly at the beginning). The combined extracts were washed (2× brine), dried (MgSO4), and concentrated under reduced pressure to yield 3.14 g of a pink solid. Recrystallization from AcOEt/heptane yielded 1.83 g (52%) of the methyl ester as slightly pink solid, m.p. 143-145° C.

$^1$H NMR (DMSO-$d_6$): δ 1.91 (m, 2H), 2.47-2.62 (m, 4H), 2.67 (m, 2H), 3.41 (m, 2H), 3.59 (s, 3H), 11.87 (s, 1H).

Step 2: Saponification:

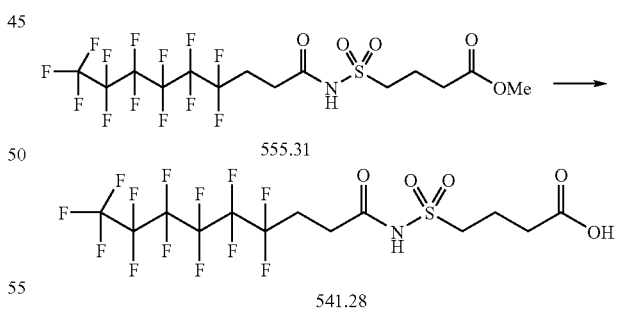

To a suspension of the methyl ester (1.11 g, 2.0 mmol) in MeOH (7.0 ml) was added a solution of NaOH (0.54 g, 13.5 mmol) in water (1.0 ml). The mixture was stirred at room temperature for 3 h 15 min. A mixture of water (30 ml) and 1N HCl (20 ml) was added, and the product was isolated by filtration. Recrystallization from MeCN (approx 5 ml) at −20° C. yielded 0.77 g (71%) of the title acid as colorless solid. M.p.: 175-180° C. $^1$H NMR (DMSO-$d_6$): δ 1.88 (m, 2H), 2.38 (t, J=7 Hz, 2H), 2.45-2.62 (m, 2H), 2.66 (m, 2H), 3.39 (m, 2H), 11.85 (s, 1H), 12.24 (s, 1H).

Example 6

N$^{\delta 17}$-(lauroylsulfamoyl)benzyl-[Glu$^3$,Gln$^{17}$]GLP-2 (1-33)

Step 1: N-Dodecanoyl-4-methylbenzenesulfonamide

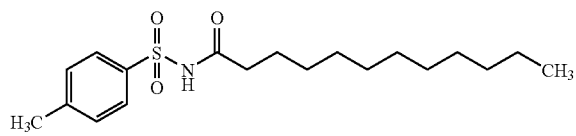

A solution of p-toluenesulfonic amide (980 mg, 5.7 mmol) and lauric anhydride (3.29 g, 8.59 mmol) in acetonitrile (100 ml) was heated to 60° C. Concentrated sulphuric acid (0.009 ml, 0.17 mmol) was added. The reaction mixture was heated to 60° C. for 1 h, and was subsequently left for 16 h at room temperature. Water (300 ml) was added. The precipitation was isolated by filtration. It was suspended in heptane. The solid was isolated by filtration to give 2.63 g of N-dodecanoyl-4-methylbenzenesulfonamide.

$^1$H NMR (DMSO-d$_6$) δ 0.85 (t, 3H); 1.00-1.45 (m, 18H); 2.20 (t, 2H); 2.40 (s, 3H); 7.40 (d, 2H); 7.80 (d, 2H); 11.90 (br, 1H).

Step 2: 4-Bromomethyl-N-(dodecanoyl)benzenesulfonamide

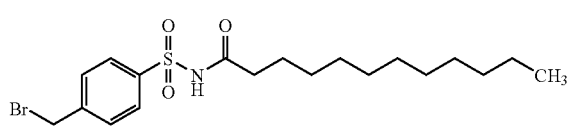

At 80° C., N-bromosuccinimide (1.43 g, 8.06 mmol) and dibenzoylperoxide (62 mg, 0.25 mmol) were added successively to a solution of N-dodecanoyl-4-methylbenzenesulfonamide (3 g, 8.48 mmol) in tetrachloromethane (75 ml). The reaction mixture was heated for 1 h to 80° C. Another portion of dibenzoylperoxide (100 mg, 0.41 mmol) was added. The reaction mixture was heated another 2 h to 80° C. It was cooled to room temperature and left for 16 h. Ethyl acetate (100 ml) and heptane (100 ml) were added. The solid was removed by filtration. The solvent was removed from the filtrate to give 4.19 g of crude 4-bromomethyl-N-(dodecanoyl)benzenesulfonamide, which was used for the next step, without further purification.

$^1$H NMR (DMSO-d$_6$) δ 0.80 (t, 3H); 1.00-1.90 (m, 18H); 3.35 (m, 2H); 4.80 (s, 2H); 7.70 (d, 2H); 7.90 (d, 2H); 11.1 (br, 1H).

Step 3: (4-(Dodecanoylsulfamoyl)benzyl)carbamic acid tert-butyl ester

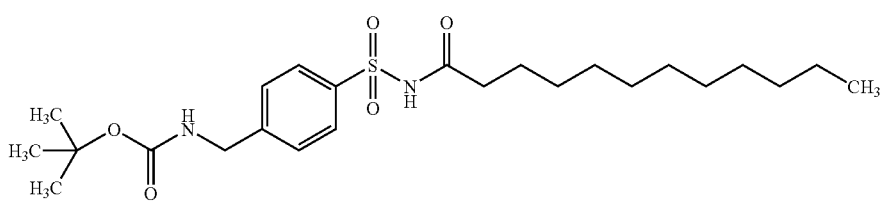

A solution of 4-bromomethyl-N-(dodecanoyl)benzenesulfonamide (2.1 g, 4.86 mmol) in N,N-dimethylformamide (20 ml) was added dropwise to a mixture of 25% aqueous ammonia (4 ml) and N,N-dimethylformamide (10 ml). The reaction mixture was stirred for 1 h at room temperature. The solvent was removed in vacuo. The residue was dissolved in 1N aqueous sodium hydroxide (25 ml, 25 mmol) and tetrahydrofuran (25 ml). Di-tert-butyl dicarbonate (1.88 g, 8.63 mmol) was added. The reaction mixture was stirred for 16 h at room temperature. It was diluted with ethyl acetate (100 ml) and washed with a 10% aqueous solution of sodium hydrogensulphate (100 ml). The aqueous phase was extracted with ethyl acetate (2×50 ml). The combined organic layers were washed with a saturated aqueous solution of sodium hydrogencarbonate (100 ml) and dried over sodium sulphate. The solvent was removed in vacuo. The crude product was purified by flash chromatography on silica (40 g), using ethyl acetate/heptane (1:2) as eluent, to give 170 mg of (4-(dodecanoylsulfamoyl)benzyl)carbamic acid tert-butyl ester.

$^1$H NMR (CDCl$_3$) δ 0.85 (t, 3H); 1.10-1.70 (m, 18H); 2.25 (t, 2H); 4.40 (d, 2H); 5.00 (br, 1H); 7.45 (d, 2H); 8.05 (d, 2H); 8.15 (br, 1H).

Step 4: 4-Aminomethyl-N-(dodecanoyl)benzenesulfonamide

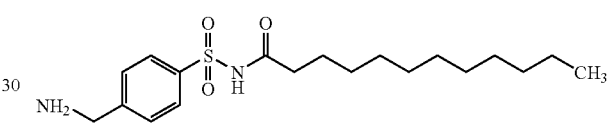

Trifluoroacetic acid (25 ml) was at room temperature added to a solution of (4-(dodecanoylsulfamoyl)benzyl)carbamic acid tert-butyl ester (170 mg, 0.40 mmol) in dichloromethane (25 ml). The reaction mixture was stirred for 1 h at room temperature. The solvents were removed in vacuo. The residue was dissolved in dichloromethane (40 ml) and the solvent was removed in vacuo. The latter procedure was repeated once to give 0.19 g of the trifluoroacetic salt of 4-aminomethyl-N-(dodecanoyl)benzenesulfonamide.

$^1$H NMR (DMSO-d$_6$) δ 0.85 (t, 3H); 1.05-1.50 (m, 18H); 2.20 (t, 2H); 4.10 (s, 2H); 7.70 (d, 2H); 7.95 (d, 2H); 8.25 (br, 3H); 12.10 (br, 1H).

Step 5:

A resin-bound peptide with the sequence of [Glu$^3$,Glu$^{17}$]GLP-2, in which the aspartic acids were protected as tert-butyl esters, the threonines were protected as tert-butyl ethers, the lysines were protected as tert-butyl carbamates, the glutamine was protected as tert-butyl amide, the tryptophane was protected as tert-butyl carbamate, the asparagines were protected as tert-butyl amide, the arginine was protected as pentamethylchromanylsulfonyl-derivative, the glutamic acid at position 17 was protected as 1-methyl-1-phenylethyl ester, the glutamic acids at positions 3 and 9 were protected as tert-butyl esters, and the histidine was protected on both the side chain and the alpha-amino group as tert-butyl carbamate, on a Wang resin, utilizing standard FMOC-chemistry on a automatic peptide-synthesizer. The resin was treated five times with a 2% solution of trifluoroacetic acid and 2% of triisopropylislane in dichloromethane (10 ml) for 10 min. The resin was washed with N-methylpyrrolidinone (3×10 ml) and dichloromethane (3×10 ml). A solution of 1-hydroxybenzotirazole (32 mg, 0.21 mmol) in N-methylpyrrolidinone (7 ml) was added. A solution of the trifluoroacetic salt of 4-aminomethyl-N-(dodecanoyl)benzenesulfonamide (202 mg, 0.42 mmol) in dichloromethane (7 ml) was added. Diisopropylcarbodiimide (0.033 ml, 0.21 mmol) and ethyldiisopropylamine (0.179 ml, 1.05 mmol) were added successively. The mixture was shaken for 16 h at room temperature. The liquid was removed. The resin was washed with N-methylpyrrolidinone (3×10 ml) and subsequently with dichloromethane (5×10 ml). A mixture of trifluoroacetic acid (10.6 ml), water (0.265 ml) and triisopropylsilane (0.265 ml) was added to the resin. The resin was shaken for 1.5 h at room temperature. The liquid was collected and concentrated to approx. 3 ml. Ether (50 ml) was added. The precipitation was isolated by centrifugation and decantation. The crude product was purified by HPLC, using a C18 column and applying a gradient of 30-55% acetonitrile in water in a 0.1% trifluoroacetic acid buffer to give the title compound. The mass spectrum was in accordance with the expected product.

MS: 1383; 1038. HPLC: 10.35 min (Method 02-b4-3)

HPLC-Method 02-b4-3:

The RP-analyses was performed using an Alliance Waters 2695 system fitted with a Waters 2487 dualband detector. UV detections were collected using a Symmetry300 C18, 3.5 um, 3.6 mm×150 mm column. The compounds are eluted with a linear gradient of 5-90% acetonitrile, 90-0% water, and 5% trifluoroacetic acid (1.0%) in water over 15 minutes at a flow-rate of 1.0 min/min.

The invention claimed is:

1. A method of increasing intravascular half-life of an agent, said method comprising converting said agent into a compound of general formula (I):

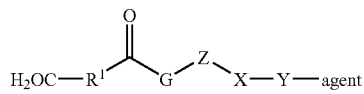

(I)

by reacting said agent with a compound of general formula

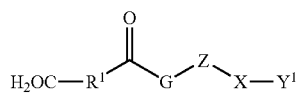

(III)

wherein
R$^1$—CO$_2$H can bind reversibly to a plasma protein and R$^1$ is selected from
C$_{1-30}$-alkyl, optionally substituted with one or more —CO$_2$H, —SO$_3$H, —PO$_2$OH, —SO$_2$NH$_2$, —NH$_2$, —OH, —SH, halogen, or aryl, said aryl optionally substituted with —CO$_2$H, —SO$_3$H, —PO$_2$OH, —SO$_2$NH$_2$, —NH$_2$, —OH, —SH, or halogen, or
C$_{1-30}$-perfluoroalkyl, optionally substituted with one or more —CO$_2$H, —SO$_3$H, —PO$_2$OH, —SO$_2$NH$_2$, —NH$_2$, —OH, —SH, halogen, or aryl, said aryl optionally substituted with —CO$_2$H, —SO$_3$H, —PO$_2$OH, —SO$_2$NH$_2$, —NH$_2$, —OH, —SH, or halogen,
G is NH or CHW, wherein W is hydrogen, fluorine, cyano, nitro, C(=O)-E$^1$, S(=O)$_2$-E$^2$, S(=O)-E$^3$, aryl, or C$_{1-6}$-alkyl,
wherein E$^1$, E$^2$, and E$^3$ independently represent C$_{1-6}$-alkyl, aryl, heteroaryl, C$_{1-6}$-alkoxy, amino, C$_{1-6}$-alkyl-amino, or di-C$_{1-6}$-alkyl-amino,
Z is S=O, S(=O)$_2$, C(=O), C(=O)O, C(=O)NR$^2$, or arylene which is optionally substituted with C$_{1-6}$-alkyl, halogen, nitro, cyano, or heteroarylene, said heteroarylene optionally substituted with $C_{1-6}$-alkyl, halogen, nitro, or cyano, wherein $R^2$ represents hydrogen, cyano, or $C_{1-6}$-alkyl, X represents a bond or optionally a spacer selected from $C_1$-$C_{20}$-alkylene, arylene, heteroarylene, $C_1$-$C_{20}$-perfluoroalkylene, or combinations thereof, or $-[(CQ_2)_nA]_m(CQ_2)_p$-, or $-[(CQ_2)_nA]_m(CQ_2)_p$-$[(CQ_2)_nE]_m(CQ_2)_p$-, wherein n and m independently are 1-20 and p independently is 0-10, each A and E independently are —O—, —S—, —NR$^3$—, —N(COR$^4$)—, —PR$^5$(O)—, or P(OR$^6$)(O)—, wherein $R^3$, $R^4$, $R^5$, and $R^6$ independently represent hydrogen or $C_{1-6}$-alkyl, each Q is independently hydrogen or fluorine, $Y^1$ is a functional group capable of undergoing a bond-forming reaction with a compound to yield a compound of the general formula (I), $Y^1$ being selected from —C(=O)-L, —C(=S)-L, —NR$^2$(C=O)-L, —OC(=O)-L, —NR$^2$(C=S)-L, —C(H$_2$)-L, —C(C$_{1-6}$alkyl)(=O), —CH(=O), —S(=O)$_2$-L, NR$^2$—S(C=O)$_2$-L, —SH, —S-L, —NCO, —NCS, —NCNR$^2$, —NC, —O—NH$_2$, wherein L is a leaving group for nucleophilic displacement, L being selected from hydroxy, halide, 2,6-dichlorobenzoyl, pivaloyl, 2- or 4-nitrophenyloxy, 2,4-dinitrophenloxy, benzotriazole-1-yloxy, 4-benzotriazol-3-yloxy, $C_{1-6}$alkoxycarbonyloxy, 4-oxo-3,4-dihydro-1,2,3-benzotriazin-3-yloxy, perfluorophenyloxy, imidazolyl, 2,5-dioxopyrrolidin-1-yloxy, 1,3-dioxo-2,3-dihydro-1-H-isondol-2-yloxy, 2,4,6-trichlorophenyloxy, or azide, and wherein $R^2$ represents hydrogen, cyano, or $C_{1-6}$-alkyl, and the agent is selected from the group consisting of a GLP-1 peptide or a GLP-2 peptide.

2. The method according to claim 1, wherein $R^1$ is selected from a straight chain alkyl group, a branched alkyl group, a group which has an ω-carboxylic acid group, or a partially or completely hydrogenated cyclopentanophenanthrene skeleton.

3. The method according to claim 1, wherein $R^1$—$CO_2H$ is selected from arylacetic acids, iophenoxate or dicarboxilic acids.

4. The method according to claim 3, wherein $R^1$—$CO_2H$ is ketoprofen or 3-carboxy-4-methyl-5-propyl-2-furanpropionic acid (CMPF).

5. The method according to claim 1, wherein $R^1$ has from 6 to 40 carbon atoms.

6. The method according to claim 1, wherein $R^1$ is a peptide.

7. The method according to claim 1, wherein G is NH.

8. The method according to claim 1, wherein Z is S(=O)$_2$.

9. The method according to claim 1, wherein Q is H.

10. The method according to claim 1, wherein A and E are both —O—.

11. The method according to claim 1, wherein n is 2.

12. The method according to claim 1, wherein said agent is a glucagon-like peptide 1 (GLP-1) peptide.

13. The method according to claim 12, wherein said GLP-1 peptide is selected from GLP-1(735), GLP-1(7-36), GLP-1(7-36)-amide, GLP-1(7-37), GLP-1(7-38), GLP-1(7-39), GLP-1(7-40), GLP-1(7-41) or an analogue thereof.

14. The method according to claim 12, wherein said polypeptide is a GLP-1 peptide comprising the amino acid sequence of the formula (IV):

Xaa$_7$-Xaa$_8$-Glu-Gly-Thr-Phe-Thr-Ser-Asp-Xaa$_{16}$-Ser-Xaa$_{18}$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Trp-Leu-Xaa$_{33}$-Xaa$_{34}$-Xaa$_{35}$-Xaa$_{36}$-Xaa$_{37}$-Xaa$_{38}$-Xaa$_{39}$-Xaa$_{40}$-Xaa$_{41}$-Xaa$_{42}$-Xaa$_{43}$-Xaa$_{44}$-Xaa$_{45}$-Xaa$_{46}$       Formula (IV) (SEQ ID No: 2)

wherein

Xaa$_7$ is L-histidine, D-histidine, desamino-histidine, 2-amino-histidine, β-hydroxy-histidine, homohistidine, N$^\alpha$-acetyl-histidine, α-fluoromethyl-histidine, α-methyl-histidine, 3-pyridylalanine, 2-pyridylalanine or 4-pyridylalanine;

Xaa$_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

Xaa$_{16}$ is Val or Leu;
Xaa$_{18}$ is Ser, Lys or Arg;
Xaa$_{19}$ is Tyr or Gln;
Xaa$_{20}$ is Leu or Met;
Xaa$_{22}$ is Gly, Glu or Aib;
Xaa$_{23}$ is Gln, Glu, Lys or Arg;
Xaa$_{25}$ is Ala or Val;
Xaa$_{26}$ is Lys, Glu or Arg;
Xaa$_{27}$ is Glu or Leu;
Xaa$_{30}$ is Ala, Glu or Arg;
Xaa$_{33}$ is Val or Lys;
Xaa$_{34}$ is Lys, Glu, Asn or Arg;
Xaa$_{35}$ is Gly or Aib;
Xaa$_{36}$ is Arg, Gly or Lys;
Xaa$_{37}$ is Gly, Ala, Glu, Pro, Lys, amide or is absent;
Xaa$_{38}$ is Lys, Ser, amide or is absent.
Xaa$_{39}$ is Ser, Lys, amide or is absent;
Xaa$_{40}$ is Gly, amide or is absent;
Xaa$_{41}$ is Ala, amide or is absent;
Xaa$_{42}$ is Pro, amide or is absent;
Xaa$_{43}$ is Pro, amide or is absent;
Xaa$_{44}$ is Pro, amide or is absent;
Xaa$_{45}$ is Ser, amide or is absent;
Xaa$_{46}$ is amide or is absent;

provided that if Xaa$_{38}$, Xaa$_{39}$, Xaa$_{40}$, Xaa$_{41}$, Xaa$_{42}$, Xaa$_{43}$, Xaa$_{44}$, Xaa$_{45}$ or Xaa$_{46}$ is absent then each amino acid residue downstream is also absent.

15. The method according to claim 12, wherein said polypeptide is a GLP-1 peptide comprising the amino acid sequence of formula (V):

Xaa$_7$-Xaa$_8$-Glu-Gly-Thr-Phe-Thr-Ser-Asp-Val-Ser-Xaa$_{18}$-Tyr-Leu-Glu-Xaa$_{22}$-Xaa$_{23}$-Ala-Ala-Xaa$_{26}$-Glu-Phe-Ile-Xaa$_{30}$-Trp-Leu-Val-Xaa$_{34}$-Xaa$_{35}$-Xaa$_{36}$-Xaa$_{37}$-Xaa$_{38}$       Formula (V) (SEQ ID No: 3)

wherein

Xaa$_7$ is L-histidine, D-histidine, desamino-histidine, 2-amino-histidine, β-hydroxy-histidine, homohistidine, N$^\alpha$-acetyl-histidine, α-fluoromethyl-histidine, α-methyl-histidine, 3-pyridylalanine, 2-pyridylalanine or 4-pyridylalanine;

Xaa$_8$ is Ala, Gly, Val, Leu, Ile, Lys, Aib, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

Xaa$_{18}$ is Ser, Lys or Arg;
Xaa$_{22}$ is Gly, Glu or Aib;
Xaa$_{23}$ is Gln, Glu, Lys or Arg;

Xaa$_{26}$ is Lys, Glu or Arg;
Xaa$_{30}$ is Ala, Glu or Arg;
Xaa$_{34}$ is Lys, Glu or Arg;
Xaa$_{35}$ is Gly or Aib;
Xaa$_{36}$ is Arg or Lys;
Xaa$_{37}$ is Gly, Ala, Glu or Lys;
Xaa$_{38}$ is Lys, amide or is absent.

16. The method according to claim 12, wherein said GLP-1 peptide is selected from the group consisting of Arg$^{34}$GLP-1(7-37),
Lys$^{38}$Arg$^{26,34}$GLP-1(7-38), Lys$^{38}$Arg$^{26,34}$GLP-1(7-38)-OH, Lys$^{36}$Arg$^{26,34}$GLP-1(7-36),
Aib$^{8,22,35}$GLP-1(7-37), Aib$^{8,35}$GLP-1(7-37), Aib$^{8,22}$GLP-1(7-37),
Aib$^{8,22,35}$Arg$^{26,34}$Lys$^{38}$GLP-1(7-38), Aib$^{8,35}$Arg$^{26,34}$Lys$^{38}$ GLP-1(7-38),
Aib$^{8,22}$Arg$^{26,34}$Lys$^{38}$GLP-1(7-38), Aib$^{8,22,35}$Arg$^{26,34}$Lys$^{38}$ GLP-1(7-38),
Aib$^{8,35}$Arg$^{26,34}$Lys$^{38}$GLP-1(7-38), Aib$^{8,22,35}$Arg$^{26}$ Lys$^{38}$GLP-1(7-38),
Aib$^{8,35}$Arg$^{26}$Lys$^{38}$GLP-1(7-38), Aib$^{8,22}$Arg$^{26}$Lys$^{38}$GLP-1(7-38),
Aib$^{8,22,35}$Arg$^{34}$Lys$^{38}$GLP-1(7-38), Aib$^{8,35}$Arg$^{34}$Lys$^{38}$ GLP-1(7-38), Aib$^{8,22}$Arg$^{34}$Lys$^{38}$GLP-1(7-38),
Aib$^{8,22,35}$Ala$^{37}$Lys$^{38}$GLP-1(7-38), Aib$^{8,35}$Ala$^{37}$Lys$^{38}$ GLP-1(7-38), Aib$^{8,22}$Ala$^{37}$Lys$^{38}$GLP-1(7-38),
Aib$^{8,22,35}$Lys$^{37}$GLP-1(7-37), Aib$^{8,35}$Lys$^{37}$GLP-1(7-37) and Aib$^{8,22}$Lys$^{37}$GLP-1(7-38).

17. The method according to claim 16, wherein said GLP-1 peptide comprises an Aib residue in position 8.

18. The method according to claim 15, wherein said GLP-1 peptide is attached to Y via the amino acid residue in position 23, 26, 34, 36, or 28 relative to the amino acid sequence SEQ ID NO: 3.

19. The method according to claim 12, wherein R$^1$—C(═O)-G-Z-X—Y— is attached to said GLP-1 peptide on the C-terminal amino acid residue of said GLP-1 peptide.

20. The method according to claim 19, wherein a second R$^1$—C(═O)-G-Z-X—Y— moiety is attached to an amino acid residue which is not the C-terminal amino acid residue.

* * * * *

UNITED STATES PATENT AND TRADEMARK OFFICE
CERTIFICATE OF CORRECTION

PATENT NO. : 7,897,560 B2
APPLICATION NO. : 11/384129
DATED : March 1, 2011
INVENTOR(S) : Dorwald et al.

It is certified that error appears in the above-identified patent and that said Letters Patent is hereby corrected as shown below:

Column 47, Claim 13, Line 62: change "GLP-1 (735)" to read --GLP-1 (7-35)--.

Column 50, Claim 18, Line 12: change "28" to read --38--.

Signed and Sealed this
Fourteenth Day of June, 2011

David J. Kappos
*Director of the United States Patent and Trademark Office*